United States Patent [19]
Feldhaus et al.

[11] Patent Number: 6,083,751
[45] Date of Patent: Jul. 4, 2000

[54] CHIMERIC RECEPTORS FOR THE GENERATION OF SELECTIVELY-ACTIVATABLE TH-INDEPENDENT CYTOTOXIC T CELLS

[75] Inventors: Andrew Lawrence Feldhaus, Lynnwood; Lori Ann Jones, Seattle, both of Wash.

[73] Assignee: Targeted Genetics Corporation, Seattle, Wash.

[21] Appl. No.: 08/549,846

[22] PCT Filed: Nov. 1, 1995

[86] PCT No.: PCT/US95/14171

§ 371 Date: Nov. 1, 1995

§ 102(e) Date: Nov. 1, 1995

[87] PCT Pub. No.: WO96/13584

PCT Pub. Date: May 9, 1996

Related U.S. Application Data

[63] Continuation of application No. 08/480,577, Jun. 7, 1995, abandoned, which is a continuation-in-part of application No. 08/332,993, Nov. 1, 1994, abandoned.

[51] Int. Cl.⁷ .............................. C12N 5/10; A61K 35/14; C07K 14/705
[52] U.S. Cl. .................................... 435/372.3; 424/93.21; 424/93.71; 435/325; 435/347; 435/373; 530/350
[58] Field of Search .................... 435/372.3, 325, 435/347, 373; 530/350, 489; 424/93.21, 93.7

[56] References Cited

U.S. PATENT DOCUMENTS

| | | | |
|---|---|---|---|
| 5,359,046 | 10/1994 | Capon | 536/23.4 |
| 5,506,126 | 4/1996 | Seed | 435/172.3 |

FOREIGN PATENT DOCUMENTS

| | | |
|---|---|---|
| 260 880 | 3/1988 | European Pat. Off. . |
| 440 373 | 7/1991 | European Pat. Off. . |
| WO 90/13644 | 11/1990 | WIPO . |
| WO 92/00092 | 1/1992 | WIPO . |
| WO 92/08796 | 5/1992 | WIPO . |
| WO92/08796 | 5/1992 | WIPO .......................... C12N 15/65 |
| WO 93/00431 | 1/1993 | WIPO . |
| WO 94/22489 | 10/1994 | WIPO . |
| WO 94/28143 | 12/1994 | WIPO . |

OTHER PUBLICATIONS

Aruffo A and Seed B, Molecular cloning of a CD28 cDNA by a high-efficiency COS cell expression system. Proc. Natl Acad. Sci. 84:8573–8577, 1987.

Bierer BE and Hahn WC, T cell adhesion, avidity regulation and signalling: a molecular analysis of CD2, Sem Immunol. 5:249–261, 1993.

Hsiung GD "Diagnostic Virology" Yale University Press, New Haven, CT pp. 17–34 and pp. 245–272, 1982.

Yong K and Khwaja A. Luecocyte cellular adhesion molecules. Blood Rev. 4:211–225, 1990.

Nabholz M and MacDonald HR, Cytolytic T lymphocytes. Ann Rev Immunol. 1:273–306, 1983.

Pierres A, et al., Triggering CD28 molecules synergize with CD2 (T11.1 and T11.1)—mediated T cell activation. Eur J Immunol. 18:685–690, 1988.

Springer, T.A., "Adhesion receptors of the immune system", Nature. (1990) 346:425–434.

Zinkernagel et al., "MHC–restricted cytotoxic T cells: studies on the biological role of polymorphic major transplantation antigens determining T–cell restriction–specificity, function, and responsiveness" Advances in Immunology, Academic Press, Inc., (1979) pp. 51–177.

Male et al., Advanced Immunology (1987) Chapter 7, entitled "Lymphocyte and phagocyte development" pp. 7.1–7.16.

Jacobson et al., "Measles virus–specific T4⁺ human cytotoxic T cell clones are restricted by class II HLA antigens" J. Immunol. (1984) 132(2):754–757.

Gillis et al., "Long term culture of tumour–specific cytotoxic T cells" Nature (1977) 268:154–156.

Cheever et al., "Augmentation of the anti–tumor therapeutic efficacy of long–term cultured T lymphocytes by in vivo administration of purified interleukin 2" J. Exp. Med. (1977) 155:968–980.

Reddehase et al., "CD8–positive T lymphocytes specific for murine cytomegalovirus immediate–early antigens mediate protective immunity" J. Virology (1987) 61(10):3102–3108.

Alderson et al., "Interleukin 7 enhances cytolytic T lymphycyte generation and induces lymphokine–activated killer cells from human peripheral blood" J. Exp. Med. (1990) 172:577–587.

Rosenberg et al., "Use of tumor–infiltrating lymphocytes and interleukin–2 in the immunotherapy of patients with metastatic melanoma" New Engl. J. Med. (1988) 319:1676–1680.

Klarnet, et al., "Role of Interleukin–2 Activated Killer Cells in Cancer", Lotzova and Herberman, eds. CRC Press, Florida (1990) Chapter 14, pp. 199–217.

(List continued on next page.)

Primary Examiner—David Saunders
Assistant Examiner—Mary Beth Tung
Attorney, Agent, or Firm—Morrison & Foerster LLP

[57] ABSTRACT

The invention provides cytotoxic T lymphocytes that express a chimeric cell surface receptor. The chimeric receptor enables the lymphocytes to become activated and to proliferate (via a $T_H$-independent autocrine cycle) in response to adhesion between the lymphocyte and an antigen displaying cell (ADC) that might not normally activate the T cell. The chimeric receptors of the present invention comprise fusion polypeptides of the following structure:

XC—TM—IC28 wherein (XC) is an extracellular region derived from a receptor for a ligand that is expressed on the surface of an antigen-displaying cell, fused via a transmembrane region is (TM) to an intracellular region (IC28) which is derived from the intracellular region of the CD28 receptor.

12 Claims, 25 Drawing Sheets

OTHER PUBLICATIONS

Klarnet et al., "Helper–independent CD8+cytotoxic T lymphocytes express IL–1 receptors and require IL–1 for secretion of IL–2" J. Immunol. (1989) 142(7):2187–2191.

Sprent et al. "Properties of purified T cell subsets" J. Exp. Med. (1985) 162:2068–2088.

Andrus et al., "Cytotoxic T cells both produce and respond to interleukin 2" J. Exp. Med. (1984) 59:647–652.

von Boehmer et al., "LTY–22 T cell–independent functions of LYT–2+ cells stimulated with antigen or concanavalin A" J. Immunol. (1984) 133(1):59–64.

Klarnet et al., "Antigen–driven T cell clones can proliferate in vivo, eradicate dissseminated leukemia, and provide specific immunologic memory" J. Immunol. (1987) 138(11):4012–4017.

Mizuochi et al., "Role of Lymphokine–secreting CD8+ T cells in cytotoxic T lymphocyte responses against vaccinia virus" J. Immunol. (1989) 142:270–273.

Weiss, A. and Imboden, J.B., "Cell Surface Molecules and Early Events Involved in Human T. Lymphocyte Activation", Advances in Immunol. (1987) 41:1–38.

Weaver, C.T. and Unanue, E.R., "The coltimulatory function of antigen–presenting cells", Immunol. Today (1990) vol. 11, No. 2:49–54.

Jenkins, M.K. and Johnson, J.G., "Molecules involved in T–cell costimulation", Current Opinion in Immunol. (1993) 5:361–367.

Stein, P.H. et al., "The Cytoplasmic Domain of CD28 Is both Necessary and Sufficient for Costimulation of Interlockin–2 Secretion and Association with Phosphatidylinositol 3'–Kinase", Molecular and Cellular Biology (1994) vol. 14, No. 5:3392–3402.

June, C.H. et al., "Role of the CD28 receptor in T–cell activation", Immunol. Today (1990) vol. 11, No. 6:211–216.

Allison, J.P., "CD28–B7 interactions in T–cell activation", Current Opinion in Immunol. (1994) 6:414–419.

Vandenberghe, P. et al., "In situ expression of B7/BB1 on antigen–presenting cells and activated B cells: an immunohistochemical study", Int. Immunol. (1993) 5:317.

Azuma, M. et al., "B70 antigen is a second ligand for CTLA–4 and CD28", Nature (1993) 366:76–79.

Freeman G.J.n et al., "Cloning of B7–2: A CTLA–4 Counter–Receptor That Costimulates Human T Cell Proliferation", Science (1994) 262:909–911.

Collins, T.L. et al., "Adhesion receptors in lymphocyte activation", Current Opinions in Immunology (1994) 6:385–393.

Brooks, C.G. et al., "Lymphokine–Driven "Differentiation" of Cytotoxic T–Cell Clones into Cells with NK–Like Specificity: Correlations with Display of Membrane Macromolecules", Immunol. Rev. (1983) 72:43–72.

Seed, B. and Aruffo, A., "Molecular cloning of the CD2 antigen the T–cell erythrocyte receptor, by a rapid immunoselection procedure", Proc. Natl. Acad. Sci. USA (1987) 84:3365–3369.

Larson, R.S. et al., "Primary Structure of the Leukocyte Function–associated Molecule–1 α Subunit: an Integrin with an Embedded Domain Defining a Protein Superfamily", J. Cell. Biol. (1989) 108:703–712.

Kishimoto, T.K. et al., "Cloning of the β Subunit of the Leukocyte Adhesion Proteins: Homology to an Extracellular Matrix Receptor Defines a Novel Supergene Family", Cell (1987) 48:681690.

Lupton, S.D. et al., "Dominant Positive and Negative Selection Using a Hygromycin Phosphotransferase–Thymidine Kinase Fusion Gene", Mol. and Cell Biology (1991) 11:3374–3378.

Prasad, K.V.S. et al., "T–cell antigen CD28 interacts with the lipid kinase phosphatidylinositol 3–kinase by a cytoplasmic Tyr(P)–Met–Xaa–met motif", PNAS (1994) 91:2834–2838.

Lu, T. et al., "CD28 signal transduction: tyrosine phosphorylation and receptor association of phosphoinositide–3 kinase correlation with $Ca^{2+}$–independent costimulatory activity", Eur. J. Immunol. (1994) 24:2732–2739.

Pagés, F. et al., "Binding of phosphatidyl–inositol–3–OH kinase to CD28 is required for T–cell signalling", Nature (1994) 369:327–328.

Fig. 2A

| Fig. 2A |
|---------|
| Fig. 2B |

```
1    gGATCCCCCGGGCTGCAGGAATTCCCTAAGATGAGCTTTCCATGTAAATTTGTAGCCAGC     60
     -----+---------+---------+---------+---------+---------+
     CCTAGGGGGCCCGACGTCCTTAAGGGATTCTACTCGAAAGGTACATTTAAACATCGGTCG

61   TTCCTTCTGATTTTCAATGTTTCTTCCAAAGGTGCAGTCTCCAAAGAGATTACGAATGCC    120
     -----+---------+---------+---------+---------+---------+
     AAGGAAGACTAAAAGTTACAAAGAAGTTTCCACGTCAGAGGTTTCTCTAATGCTTACGG

121  TTGGAAACCTGGGGTGCCTTGGGTCAGGACATCAACTTGGACATTCCTAGTTTTCAAATG    180
     -----+---------+---------+---------+---------+---------+
     AACCTTTGGACCCCACGGAACCCAGTCCTGTAGTTGAACCTGTAAGGATCAAAAGTTTAC

181  AGTGATGATATTGACGATATAAAATGGGAAAAACTTCAGACAAGAAAAAGATTGCACAA    240
     -----+---------+---------+---------+---------+---------+
     TCACTACTATAACTGCTATATTTTACCCTTTTTGAAGTCTGTTCTTTTTCTAACGTGTT

241  TTCAGAAAAGAGAAAGAGACTTTCAAGGAAAAAGATACACATATAAGCTATTTAAAAATGGA    300
     -----+---------+---------+---------+---------+---------+
     AAGTCTTTTCTCTTTCTGAAAGTTCCTTTTTCTATGTATATTCGATAAATTTTTACCT

301  ACTCTGAAAATTAAGCATCTGAAGACCGATGATCAGGATATCTACAAGGTATCAATATAT    360
     -----+---------+---------+---------+---------+---------+
     TGAGACTTTTAATTCGTAGACTTCTGGCTACTAGTCCTATAGATGTTCCATAGTTATATA

361  GATACAAAAGGAAAAATGTGTTGGAAAAATATTTGATTTGAAGATTCAAGAGAGGGTC    420
     -----+---------+---------+---------+---------+---------+
     CTATGTTTCCTTTTTTACAACAACCTTTTTTATAAACTAAACTTCTAAGTTCTCTCCCAG
```

```
421  TCAAAACCAAAGATCTCCTGGACTTGTATCAACACAACCCTGACCTGTGAGGTAATGAAT  480
     ----+----|----+----|----+----|----+----|----+----|----+----|
     AGTTTTGGTTTCTAGAGGACCTGAACATAGTTGTGTTGGGACTGGACACTCCATTACTTA

481  GGAACTGACCCCGAATTAAACCTGTATCAAGATGGGAAACATCTAAAACTTTCTCAGAGG  540
     ----+----|----+----|----+----|----+----|----+----|----+----|
     CCTTGACTGGGGCTTAATTTGGACATAGTTCTACCCTTTGTAGATTTTGAAAGAGTCTCC

541  GTCATCACACACAAGTGGACCACCAGCCTGAGTGCAAAATTCAAGTGCACAGCAGGGAAC  600
     ----+----|----+----|----+----|----+----|----+----|----+----|
     CAGTAGTGTGTGTTCACCTGGTGGTCGGACTCACGTTTTAAGTTCACGTGTCGTCCCTTG

601  AAAGTCAGGCAAGGAATCCAGTGTCGAGCCTGTCAGCTGTCCAGAGAAAGGTATCGATTT  660
     ----+----|----+----|----+----|----+----|----+----|----+----|
     TTTCAGTCGTTCCTTAGGTCACAGCTCGGACAGTCGACAGGTCTCTTTCCATAGCTAAAA

661  TGGGTGCTGGTGGTGGTTGGTGGAGTCCTGGCTTGCTATAGCTTGCTAGTAACAGTGGCC  720
     ----+----|----+----|----+----|----+----|----+----|----+----|
     ACCCACGACCACCACCAACCACCTCAGGACCGAACGATATCGAACGATCATTGTCACCGG

721  TTTATTATTTCTGGGTGAGGAGTAAGAGAGGAGCAGGCTCCTGCACAGTGACTACATGAAC  780
     ----+----|----+----|----+----|----+----|----+----|----+----|
     AAATAATAAAGACCCACTCCTCATTCTCCTCGTCCGAGGACGTGTCACTGATGTACTTG

781  ATGACTCCCCGCCGCCCCCGCCGGGCCCACCCGCAAGCATTACCAGCCCTATGCCCACGC  840
     ----+----|----+----|----+----|----+----|----+----|----+----|
     TACTGAGGGGCGGCGGGGGCGGCCCGGGTGGGCGTTCGTAATGGTCGGGATACGGGTGCG

841  GACTTCGCAGCCTATCGCTCCTGACACGGGTCGAC  875
     ----+----|----+----|----+----|----
     CTGAAGCGTCGGATAGCGAGGACTGTGCCCAGCTG
```

| Fig. 3A |
|---------|
| Fig. 3B |
| Fig. 3C |
| Fig. 3D |

Fig. 3A

```
  1  TCTAGAGGAT CCCCTCTTTC ACCCTGTCTA GGTTGCCAGC AAATCCCACG
 51  GGCCTCCTGA CGCTGCCCCT GGGGCCACAG GTCCCTCGAG TGCTGGAAGG
101  ATGAAGGATT CCTGCATCAC TGTGATGGCC ATGGCCCTGC TGTCTGGGTT
151  CTTTTTCTTC GCGCCGGCCT CGAGCTACAA CCTGGACGTG CGGGGCGCGC
201  GGAGCTTCTC CCCACCGCGC GCCGGGAGGC ACTTTGGATA CCCGCGTCCTG
251  CAGGTCGGAA ACGGGGTCAT CGTGGGAGCT CCAGGGGAGG GAACAGCAC
301  AGGAAGCCTC TATCAGTGCC AGTCGGGCAC AGGACACTGC CTGCCAGTCA
351  CCCTGAGAGG TTCCAACTAT ACCTCCAAGT ACTTGGGAAT GACCTTGGCA
401  ACAGACCCCA CAGATGGAAG CATTTTGGCC TGTGACCCTG GGCTGTCTCG
451  AACGTGTGAC CAGAACACCT ATCTGAGTGG CCTGTGTTAC CTCTTCCGCC
501  AGAATCTGCA GGGTCCCATG CTGCAGGGGC GCCCTGGTTT TCAGGAATGT
551  ATCAAGGGCA ACGTAGACCT GGTATTTCTG TTTGATGGTT CGATGAGCTT
601  GCAGCCAGAT GAATTTCAGA AAATTCTGGA CTTCATGAAG GATGTGATGA
651  AGAAACTCAG CAACACTTCG TACCAGTTTG CTGCTGTTCA GTTTTCCACA
701  AGCTACAAAA CAGAATTTGA TTTCTCAGAT TATGTTAAAT GGAAGGACCC
751  TGATGCTCTG CTGAAGCATG TAAAGCACAT GTTGCTGTTG ACCAATACCT
801  TTGGTGCCAT CAATTATGTC GCGACAGAGG TGTTCCGGGA GGAGCTGGGG
851  GCCCGGCCAG ATGCCACCAA AGTGCTTATC ATCATCACGG ATGGGGAGGC
```

```
 901  CACTGACAGT GGCAACATCG ATGCGGCCAA AGACATCATC CGCTACATCA
 951  TCGGGATTGG AAAGCATTTT CAGACCAAGG AGAGTCAGGA GACCCTCCAC
1001  AAATTTGCAT CAAAACCCGC GAGCGAGTTT GTGAAAATTC TGGACACATT
1051  TGAGAAGCTG AAAGATCTAT TCACTGAGCT GCAGAAGAAG ATCTATGTCA
1101  TTGAGGGCAC AAGCAAACAG GACCTGACTT CCTTCAACAT GGAGCTGTCC
1151  TCCAGCGGCA TCAGTGCTGA CCTCAGCAGG GGCCATGCAG TCGTGGGGGC
1201  AGTAGGAGCC AAGGACTGGG CTGGGGGCTT TCTTGACCTG AAGGCAGACC
1251  TGCAGGATGA CACATTTATT GGGAATGAAC CATTGACACC AGAAGTGAGA
1301  GCAGGCTATT TGGGTTACAC CGTGACCTGG CTGCCCCTCCC GGCAAAAGAC
1351  TTCGTTGCTG GCCTCGGGAG CCCCTCGATA CCAGCACATG GGCCGAGTGC
1401  TGCTGTTCCA AGAGCCACAG GGCGGAGGAC ACTGGAGCCA GGTCCAGACA
1451  ATCCATGGGA CCCAGATTGG CTCTTATTTC GGTGGGGAGC TGTGTGGCGT
1501  CGACCTGGAC CAAGATGGGG AGACAGAGCT GCTGCTGATT GGTGCCCCAC
1551  TGTTCTATGG GGAGCAGAGA GGAGGCCCGG TGTTTATCTA CCAGAGAAGA
1601  CAGTTGGGGT TTGAAGAAGT CTCAGAGCTG CAGGGGGACC CCGGCTACCC
1651  ACTCGGGCGG CCATCACTGC TCTGACAGAC ATCAACGGCG
1701  ATGGGCTGGT AGACGTGGCT GTGGGGCCC CTCTGGAGGA GCAGGGGGCT
1751  GTGTACATCT TCAATGGGAG GCACGGGGGG CTTAGTCCCC AGCCAAGTCA
```

Fig. 3B

```
1801  GCGGATAGAA GGGACCCAAG TGCTCTCAGG AATTCAGTGG TTTGGACGCT
1851  CCATCCATGG GGTGAAGGAC CTTGAAGGGG ATGGCTTGGC AGATGTGGCT
1901  GTGGGGGCTG AGAGCCAGAT GATCGTGCTG AGCTCCCGGC CCGTGGTGGA
1951  TATGGTCACC CTGATGTCCT TCTCTCCAGC TGAGATCCCA GTGCATGAAG
2001  TGGAGTGCTC CTATTCAACC AGTAACAAGA TGAAAGAAGG AGTTAATATC
2051  ACAATCTGTT TCCAGATCAA GTCTCTCTAC CCCCAGTTCC AAGGCCCGCCT
2101  GGTTGCCAAT CTCACTTACA CTCTGCAGCT GGATGGCCAC CGGACCAGAA
2151  GACGGGGGTT GTCCCAGGA GGGAGACATG AACTCAGAAG GAATATAGCT
2201  GTCACCACCA GCATGTCATG CACTGACTTC TCATTTCATT TCCCGGTATG
2251  TGTTCAAGAC CTCATCTCCC CCATCAATGT TTCCCTGAAT TTCTCTCTTT
2301  GGGAGGAGGA AGGGACACCG AGGGACCAAA GGGCGCAGGG CAAGGACATA
2351  CCGCCCATCC TGAGACCCTC CCTGCACTCG GAAACCTGGG AGATCCCTTT
2401  TGAGAAGAAC TGTGGGGAGG ACAAGAAGTG TGAGGCAAAC TTGAGAGTGT
2451  CCTTCTCTCC TGCAAGATCC AGAGCCCTGC GTCTAACTGC TTTTGCCAGC
2501  CTCTCTGTGG AGCTGAGCCT GAGTAACTTG GAAGAAGATG CTTACTGGGT
2551  CCAGCTGGAC CTGCACTTCC CCCCGGGACT CTCCTTCCCG CAAGGTGGAGA
2601  TGCTGAAGCC CCATAGCCAG ATACCTGTGA GCTGCCAGGA GCTTCCTGAA
2651  GAGTCCAGGC TTCTGTCCAG GGCATTATCT TGCAATGTGA GCTCTCCCAT
```

Fig. 3C

```
2701  CTTCAAAGCA GGCCACTCGG TTGCTCTGCA GATGATGTTT AATACACTGG
2751  TAAACAGCTC CTGGGGGAC  TCGGTTGAAT TGCACGCCAA TGTGACCTGT
2801  AACAATGAGG ACTCAGACCT CCTGGAGGAC AACTCAGCCA CTACCATCAT
2851  CCCCATCCTG TACCCCATCA ACATCCTCAT CCAGGACCAA GAAGACTCCA
2901  CACTCTATGT CAGTTTCACC CCCAAAGGCC CCAAGTCCA  CCAAGTCAAG
2951  CACATGTACC AGGTGAGGAT CCAGCCTTCC ATCCACGACC ACAACATACC
3001  CACCCTGGAG GCTGTGGTTG GGGTGCCACA GCCTCCCAGC GAGGGGCCCA
3051  TCACACACCA GTGGAGCGTG CAGATGGAGC CTGCCCGTGCC CTGCCACTAT
3101  GAGGATCTGG AGAGGCTCCC GGATGCCAGT CTTCAGGCA  GGAGATCCTC GTCCAAGTGA
3151  CCTGTTCCGC TGCCCTGTTG TCTTCAGGCA GGAGAGATCG AGGCCTCTTC CATGTTCAGC
3201  TCGGGACTCT GGAGCTGGTG GGAGAGATCG AGGCCTCTTC CATGTTCAGC
3251  CTCTGCAGCT CCCTCTCCAT CTCCTTCAAC AGCAGCAAGC ATTTCCACCT
3301  CTATGGCAGC AACGCCTCCC TGGCCCAGGT TGTCATGAAG GTTGACGTGG
3351  TGTATGAGAA GCAGGATTTT TGGGTGCTGG TGGTGGTTGG TGGAGTCCTG
3401  GCTTGCTATA GCTTGCTAGT AACAGTGGCC TTTATTATTT TCTGGGTGAG
3451  GAGTAAGAGG AGCAGGCTCC TGCACAGTGA CTACATGAAC ATGACTCCCC
3501  GCCGCCCCGG GCCCACCCGC AAGCATTACC AGCCCTATGC CCCACCACGC
3551  GACTTCGCAG CCTATCGCTC CTGACACGGG GTACC
```

Fig. 3D

| | | | | |
|---|---|---|---|---|
| | Fig. 4A | | | |
| | Fig. 4B | | | |
| | Fig. 4C | | | |

```
  1  TCTAGACTCG AGCAGGGCAG ACTGGTAGCA AAGCCCCCAC GCCCAGCCAG
 51  GAGCACCGCC GCGGACTCCA GCACACCGAG GGACATGCTG GGCCTGCGCC
101  CCCCACTGCT CGCCCTGGTG GGGCTGCTCT CCCTCGGGTG CGTCCTCTCT
151  CAGGAGTGCA CGAAGTTCAA GGTCAGCAGC TGCCGGGAAT GCATCGAGTC
201  GGGGCCCGGC TGCACCTGGT GCCAGAAGCT GAACTTCACA GGGCCGGGGG
251  ATCCTGACTC CATTCGCTGC GACACCCGGC CACAGCTGCT CATGAGGGGC
301  TGTGCGGCTG ACGACATCAT GGACCCCACA AGCCTCGCTG AAACCCAGGA
351  AGACCACAAT GGGGGCCAGA AGCAGCTGTC CCCACAAAAA GTGACGCTTT
401  ACCTGCGACC AGGCCAGGCA GCAGCGTTCA ACGTGACCTT CCGGCGGGCC
451  AAGGGCTACC CCATCGACCT GTACTATCTG ATGGACCTCT CCTACTCCAT
501  GCTTGATGAC CTCAGGAATG TCAAGAAGCT AGGTGGCGAC CTGCTCCGGG
551  CCCTCAACGA GATCACCGAG TCCGGCCGCA TTGGCTTCGG GTCCTTCGTG
601  GACAAGACCG TGCTGCCGTT CGTGAACACG CACCCTGATA AGCTGCGAAA
651  CCCATGCCCC AACAAGGAGA AAGAGTGCCA GCCCCCGTTT GCCTTCAGGC
701  ACGTGCTGAA GCTGACCAAC AACTCCAACC AGTTTCAGAC CGAGGTCGGG
```

```
 751  AAGCAGCTGA TTTCCGGAAA CCTGGATGCA CCCGAGGGTG GGCTGGACGC
 801  CATGATGCAG GTCGCCGCCT GCCCGGAGGA AATCGGCTGG CGCAACGTCA
 851  CGCGGCTGCT GGTGTTTGCC ACTGATGACG GCTTCCATTT CGCGGGCGAC
 901  GGAAAGCTGG GCGCCATCCT GACCCCCAAC GACGGCCGCT GTCACCTGGA
 951  GGACAACTTG TACAAGAGGA GCAACGAATT CGACTACCCA TCGGTGGGCC
1001  AGCTGGCGCA CAAGCTGGCT GAAAACAACA TCCAGCCCAT CTTCCGGGTG
1051  ACCAGTAGGA TGGTGAAGAC CTACGAGAAA CTCACCGAGA TCATCCCCAA
1101  GTCAGCCGTG GGGGAGCTGT CTGAGGACTC CAGCAATGTG GTCCATCTCA
1151  TTAAGAATGC TTACAATAAA CTCTCCTCCA GGGTCTTCCT GGATCACAAC
1201  GCCCTCCCCG ACACCCTGAA AGTCACCTAC GACTCCTTCT GCAGCAATGG
1251  AGTGACGCAC AGGAACCAGC CCAGAGGTGA CGGCCACAGA GTGCAGATCA
1301  ATGTCCCGAT CACCTTCCAG GTGAAGGTCA CGGCCACGTG CCGGATCCAG
1351  GAGCAGTCGT TTGTCATCCG GGCGCTGGGC TTCACGGACA TAGTGACCGT
1401  GCAGGTTCTT CCCCAGTGTG AGTGCCGGTG CCGGGACCAG AGCAGAGACC
1451  GCAGCCTCTG CCATGGCAAG GGCTTCTTGG AGTGCGGCAT CTGCAGGTGT
1501  GACACTGGCT ACATTGGGAA AAACTGTGAG TGCCAGACAC AGGGCCGGAG
1551  CAGCCAGGAG CTGGAAGGAA GCTGCCGGAA GGACAACAAC TCCATCATCT
```

Fig. 4B

```
1601  GCTCAGGGCT GGGGGACTGT GTCTGCGGGC AGTGCCTGTG CCACACCAGC
1651  GACGTCCCCG GCAAGCTGAT ATACGGGCAG TACTGCGAGT GTGACACCAT
1701  CAACTGTGAG CGCTACAACG GCCAGGTCTG CGGCGGCCCG GGGAGGGGGC
1751  TCTGCTTCTG CGGGAAGTGC CGCTGCCACC CGGGCTTTGA GGGCTCAGCG
1801  TGCCAGTGCG AGAGGACCAC TGAGGGCTGC CTGAACCCCG GGCGTGTTGA
1851  GTGTAGTGGT CGTGGCCGGT GCCTGCCAAC CGTATGCGAG TGCCATTCAG
1901  GCTACCAGCT GCCTCTGTGC CAGGAGTGCC CCGGCTGCCC CTCACCCTGT
1951  GGCAAGTACA TCTCCTGCGC CGAGTGCCTG AAGTTCGAAA AGGGCCCCTT
2001  TGGGAAGAAC TGCAGCCGGG CGTGTCCCGG CCTGCAGCTG TCGAACAACC
2051  CCGTGAAGGG CAGGACCTGC AAGGAGAGGG ACTCAGAGGG CTGCTGGGTG
2101  GCCTACACGC TGGAGCAGCA GGACGGGATG GACCGCTACC TCATCTATGT
2151  GGATGAGAGC CGAGAGTGTG TGGCAGGCCC CAACGATTTT TGGGTGCTGG
2201  TGGTGGTTGG TGGAGTCCTG GCTTGCTATA GCTTGCTAGT AACAGTGGCC
2251  TTTATTATTT TCTGGGTGAG GAGTAAGAGG AGCAGGCTCC TGCACAGTGA
2301  CTACATGAAC ATGACTCCCC GCCGCCCCGG GCCCACCCGC AAGCATTACC
2351  AGCCCTATGC CCCACCACGC GACTTCGCAG CCTATCGCTC CTGACACGGG
2401  TCGAC
```

Fig. 4C

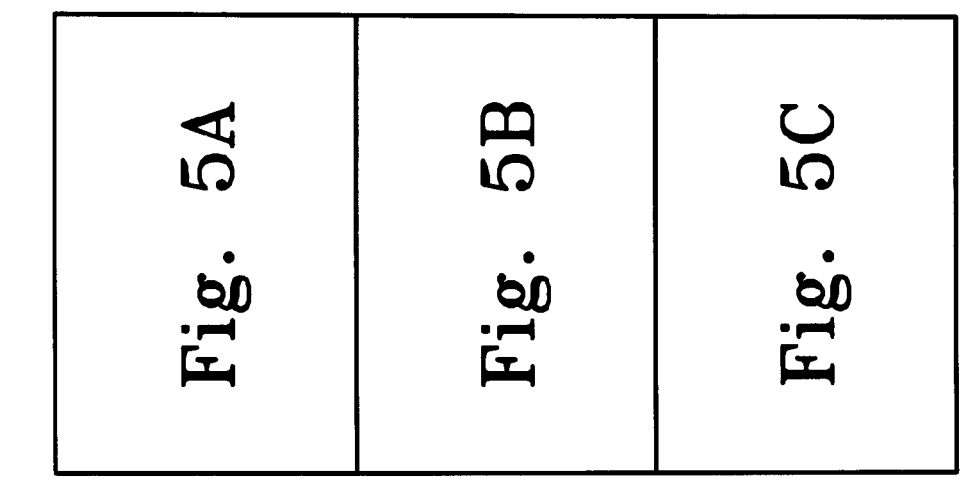

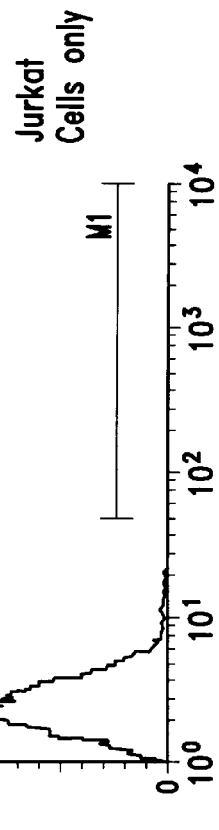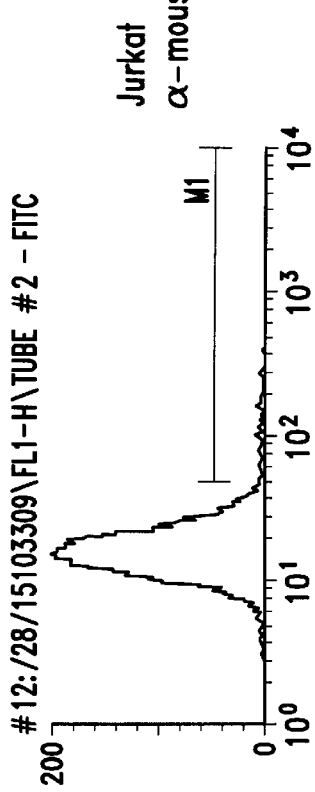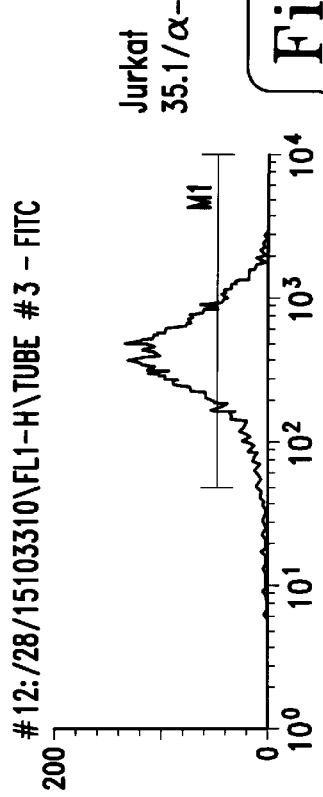
Fig. 5A

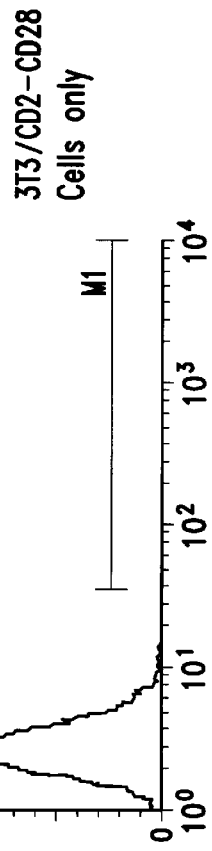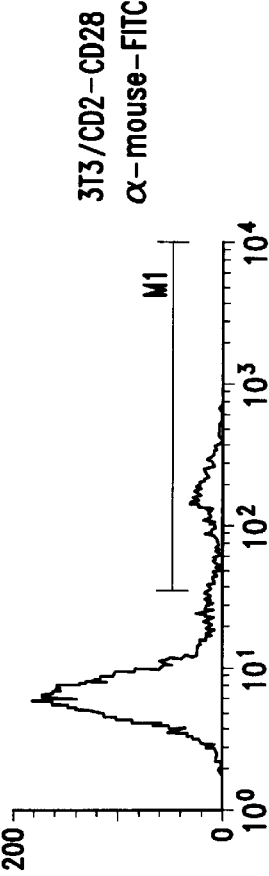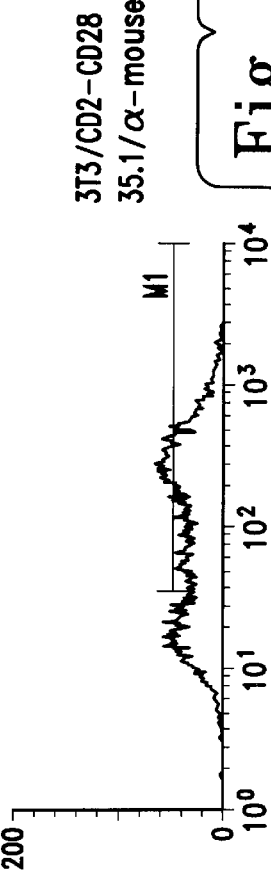
Fig. 5C

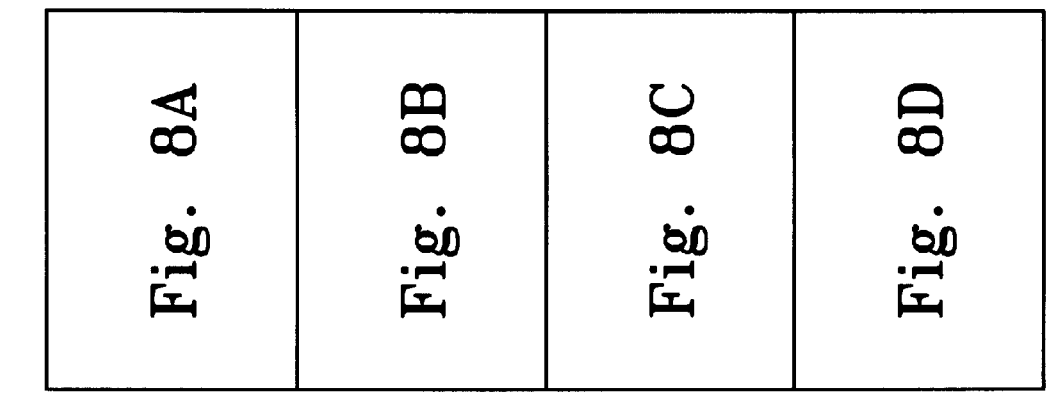

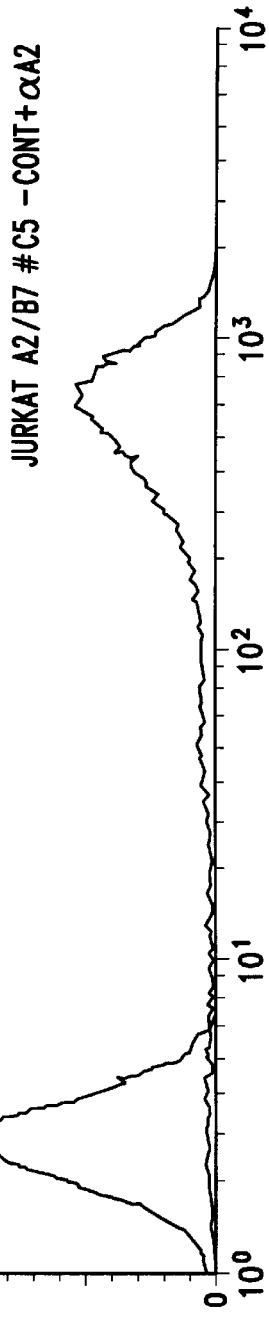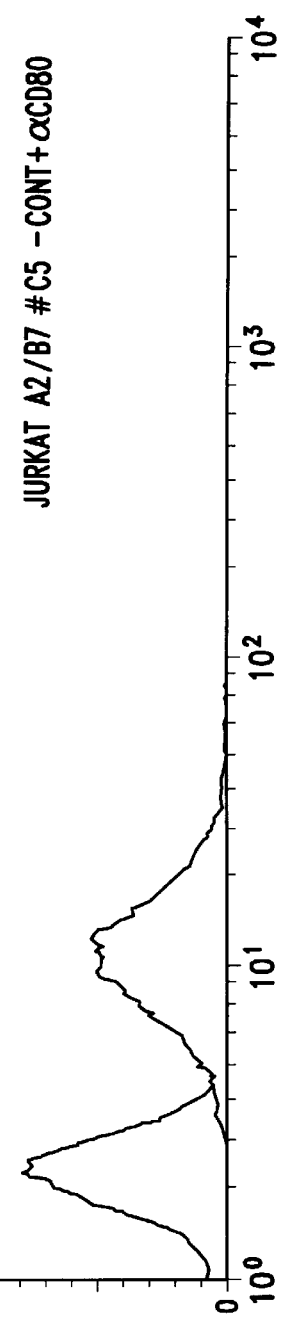
Fig. 8D

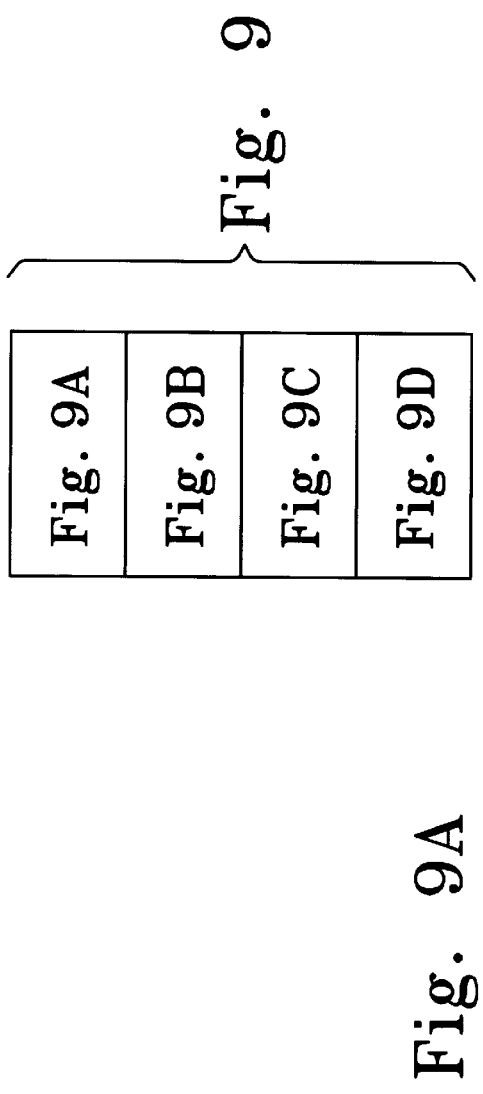
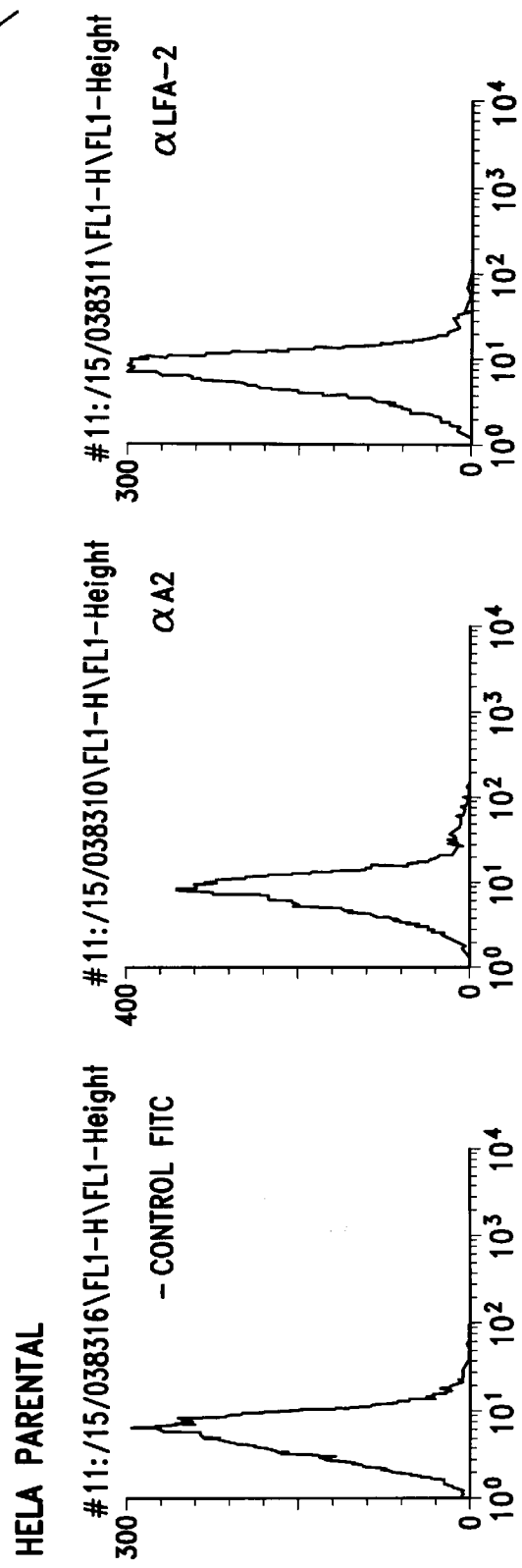
Fig. 9A

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 875 base pairs
        (B) TYPE: nucleic acid
        (C) STRANDEDNESS: single
        (D) TOPOLOGY: linear (xi) SEQUENCE DESCRIPTION: SEQ ID NO:1:

```
GGATCCCCCG GGCTGCAGGA ATTCCCTAAG ATGAGCTTTC CATGTAAATT TGTAGCCAGC         60

TTCCTTCTGA TTTTCAATGT TTCTTCCAAA GGTGCAGTCT CCAAAGAGAT TACGAATGCC        120

TTGGAAACCT GGGGTGCCTT GGGTCAGGAC ATCAACTTGG ACATTCCTAG TTTTCAAATG        180

AGTGATGATA TTGACGATAT AAAATGGGAA AAAACTTCAG ACAAGAAAAA GATTGCACAA        240

TTCAGAAAAG AGAAAGAGAC TTTCAAGGAA AAAGATACAT ATAAGCTATT TAAAAATGGA        300

ACTCTGAAAA TTAAGCATCT GAAGACCGAT GATCAGGATA TCTACAAGGT ATCAATATAT        360

GATACAAAAG GAAAAAATGT GTTGGAAAAA ATATTTGATT TGAAGATTCA AGAGAGGGTC        420

TCAAAACCAA AGATCTCCTG GACTTGTATC AACACAACCC TGACCTGTGA GGTAATGAAT        480

GGAACTGACC CCGAATTAAA CCTGTATCAA GATGGGAAAC ATCTAAAACT TTCTCAGAGG        540

GTCATCACAC ACAAGTGGAC CACCAGCCTG AGTGCAAAAT TCAAGTGCAC AGCAGGGAAC        600

AAAGTCAGCA AGGAATCCAG TGTCGAGCCT GTCAGCTGTC AGAGAAAGG TATCGATTTT        660

TGGGTGCTGG TGGTGGTTGG TGGAGTCCTG GCTTGCTATA GCTTGCTAGT AACAGTGGCC        720

TTTATTATTT TCTGGGTGAG GAGTAAGAGG AGCAGGCTCC TGCACAGTGA CTACATGAAC        780

ATGACTCCCC GCCGCCCCGG GCCCACCCGC AAGCATTACC AGCCCTATGC CCCACCACGC        840

GACTTCGCAG CCTATCGCTC CTGACACGGG TCGAC                                  875
```

(2) INFORMATION FOR SEQ ID NO:2:

(i) SEQUENCE CHARACTERISTICS:
        (A) LENGTH: 3585 base pairs
        (B) TYPE: nucleic acid
        (C) STRANDEDNESS: single
        (D) TOPOLOGY: linear (xi) SEQUENCE DESCRIPTION: SEQ ID NO:2:

```
TCTAGAGGAT CCCCTCTTTC ACCCTGTCTA GGTTGCCAGC AAATCCCACG GGCCTCCTGA         60

CGCTGCCCCT GGGGCCACAG GTCCCTCGAG TGCTGGAAGG ATGAAGGATT CCTGCATCAC        120

TGTGATGGCC ATGGCGCTGC TGTCTGGGTT CTTTTTCTTC GCGCCGGCCT CGAGCTACAA        180
```

-continued

```
CCTGGACGTG CGGGGCGCGC GGAGCTTCTC CCCACCGCGC GCCGGGAGGC ACTTTGGATA    240
CCGCGTCCTG CAGGTCGGAA ACGGGGTCAT CGTGGGAGCT CCAGGGGAGG GGAACAGCAC    300
AGGAAGCCTC TATCAGTGCC AGTCGGGCAC AGGACACTGC CTGCCAGTCA CCCTGAGAGG    360
TTCCAACTAT ACCTCCAAGT ACTTGGGAAT GACCTTGGCA ACAGACCCCA CAGATGGAAG    420
CATTTTGGCC TGTGACCCTG GCTGTCTCG AACGTGTGAC CAGAACACCT ATCTGAGTGG    480
CCTGTGTTAC CTCTTCCGCC AGAATCTGCA GGGTCCCATG CTGCAGGGGC GCCCTGGTTT    540
TCAGGAATGT ATCAAGGGCA ACGTAGACCT GGTATTTCTG TTTGATGGTT CGATGAGCTT    600
GCAGCCAGAT GAATTTCAGA AAATTCTGGA CTTCATGAAG GATGTGATGA AGAAACTCAG    660
CAACACTTCG TACCAGTTTG CTGCTGTTCA GTTTTCCACA AGCTACAAAA CAGAATTTGA    720
TTTCTCAGAT TATGTTAAAT GGAAGGACCC TGATGCTCTG CTGAAGCATG TAAAGCACAT    780
GTTGCTGTTG ACCAATACCT TTGGTGCCAT CAATTATGTC GCGACAGAGG TGTTCCGGGA    840
GGAGCTGGGG GCCCGGCCAG ATGCCACCAA AGTGCTTATC ATCATCACGG ATGGGGAGGC    900
CACTGACAGT GGCAACATCG ATGCGGCCAA AGACATCATC CGCTACATCA TCGGGATTGG    960
AAAGCATTTT CAGACCAAGG AGAGTCAGGA GACCCTCCAC AAATTTGCAT CAAAACCCGC   1020
GAGCGAGTTT GTGAAAATTC TGGACACATT TGAGAAGCTG AAAGATCTAT TCACTGAGCT   1080
GCAGAAGAAG ATCTATGTCA TTGAGGGCAC AAGCAAACAG GACCTGACTT CCTTCAACAT   1140
GGAGCTGTCC TCCAGCGGCA TCAGTGCTGA CCTCAGCAGG GGCCATGCAG TCGTGGGGGC   1200
AGTAGGAGCC AAGGACTGGG CTGGGGGCTT TCTTGACCTG AAGGCAGACC TGCAGGATGA   1260
CACATTTATT GGGAATGAAC CATTGACACC AGAAGTGAGA GCAGGCTATT TGGGTTACAC   1320
CGTGACCTGG CTGCCCTCCC GGCAAAAGAC TTCGTTGCTG GCCTCGGGAG CCCCTCGATA   1380
CCAGCACATG GGCCGAGTGC TGCTGTTCCA AGAGCCACAG GGCGGAGGAC ACTGGAGCCA   1440
GGTCCAGACA ATCCATGGA CCCAGATTGG CTCTTATTTC GGTGGGGAGC TGTGTGGCGT   1500
CGACGTGGAC CAAGATGGGG AGACAGAGCT GCTGCTGATT GGTGCCCCAC TGTTCTATGG   1560
GGAGCAGAGA GGAGGCCGGG TGTTTATCTA CCAGAGAAGA CAGTTGGGGT TGAAGAAGT   1620
CTCAGAGCTG CAGGGGGACC CCGGCTACCC ACTCGGGCGG TTTGGAGAAG CCATCACTGC   1680
TCTGACAGAC ATCAACGGCG ATGGGCTGGT AGACGTGGCT GTGGGGGCCC CTCTGGAGGA   1740
GCAGGGGGCT GTGTACATCT TCAATGGGAG GCACGGGGGG CTTAGTCCCC AGCCAAGTCA   1800
GCGGATAGAA GGGACCCAAG TGCTCTCAGG AATTCAGTGG TTTGGACGCT CCATCCATGG   1860
GGTGAAGGAC CTTGAAGGGG ATGGCTTGGC AGATGTGGCT GTGGGGGCTG AGAGCCAGAT   1920
GATCGTGCTG AGCTCCCGGC CGTGGTGGA TATGGTCACC CTGATGTCCT TCTCTCCAGC   1980
TGAGATCCCA GTGCATGAAG TGGAGTGCTC CTATTCAACC AGTAACAAGA TGAAAGAAGG   2040
AGTTAATATC ACAATCTGTT TCCAGATCAA GTCTCTCTAC CCCCAGTTCC AAGGCCGCCT   2100
GGTTGCCAAT CTCACTTACA CTCTGCAGCT GGATGGCCAC CGGACCAGAA GACGGGGGTT   2160
GTTCCCAGGA GGGAGACATG AACTCAGAAG GAATATAGCT GTCACCACCA GCATGTCATG   2220
CACTGACTTC TCATTTCATT TCCCGGTATG TGTTCAAGAC CTCATCTCCC CCATCAATGT   2280
TTCCCTGAAT TTCTCTCTTT GGGAGGAGGA AGGGACACCG AGGGACCAAA GGGCGCAGGG   2340
CAAGGACATA CCGCCCATCC TGAGACCCTC CCTGCACTCG GAAACCTGGG AGATCCCTTT   2400
TGAGAAGAAC TGTGGGGAGG ACAAGAAGTG TGAGGCAAAC TTGAGAGTGT CCTTCTCTCC   2460
TGCAAGATCC AGAGCCCTGC GTCTAACTGC TTTTGCCAGC CTCTCTGTGG AGCTGAGCCT   2520
```

-continued

```
GAGTAACTTG GAAGAAGATG CTTACTGGGT CCAGCTGGAC CTGCACTTCC CCCCGGGACT    2580

CTCCTTCCGC AAGGTGGAGA TGCTGAAGCC CCATAGCCAG ATACCTGTGA GCTGCGAGGA    2640

GCTTCCTGAA GAGTCCAGGC TTCTGTCCAG GGCATTATCT TGCAATGTGA GCTCTCCCAT    2700

CTTCAAAGCA GGCCACTCGG TTGCTCTGCA GATGATGTTT AATACACTGG TAAACAGCTC    2760

CTGGGGGAC TCGGTTGAAT TGCACGCCAA TGTGACCTGT AACAATGAGG ACTCAGACCT     2820

CCTGGAGGAC AACTCAGCCA CTACCATCAT CCCCATCCTG TACCCCATCA ACATCCTCAT    2880

CCAGGACCAA GAAGACTCCA CACTCTATGT CAGTTTCACC CCCAAAGGCC CCAAGATCCA    2940

CCAAGTCAAG CACATGTACC AGGTGAGGAT CCAGCCTTCC ATCCACGACC ACAACATACC    3000

CACCCTGGAG GCTGTGGTTG GGGTGCCACA GCCTCCCAGC GAGGGGCCCA TCACACACCA    3060

GTGGAGCGTG CAGATGGAGC CTCCCGTGCC CTGCCACTAT GAGGATCTGG AGAGGCTCCC    3120

GGATGCAGCT GAGCCTTGTC TCCCCGGAGC CCTGTTCCGC TGCCCTGTTG TCTTCAGGCA    3180

GGAGATCCTC GTCCAAGTGA TCGGGACTCT GGAGCTGGTG GGAGAGATCG AGGCCTCTTC    3240

CATGTTCAGC CTCTGCAGCT CCCTCTCCAT CTCCTTCAAC AGCAGCAAGC ATTTCCACCT    3300

CTATGGCAGC AACGCCTCCC TGGCCCAGGT TGTCATGAAG GTTGACGTGG TGTATGAGAA    3360

GCAGGATTTT TGGGTGCTGG TGGTGGTTGG TGGAGTCCTG GCTTGCTATA GCTTGCTAGT    3420

AACAGTGGCC TTTATTATTT TCTGGGTGAG GAGTAAGAGG AGCAGGCTCC TGCACAGTGA    3480

CTACATGAAC ATGACTCCCC GCCGCCCCGG GCCCACCCGC AAGCATTACC AGCCCTATGC    3540

CCCACCACGC GACTTCGCAG CCTATCGCTC CTGACACGGG GTACC                   3585
```

(2) INFORMATION FOR SEQ ID NO:3:

(i) SEQUENCE CHARACTERISTICS:
        (A) LENGTH: 2405 base pairs
        (B) TYPE: nucleic acid
        (C) STRANDEDNESS: single
        (D) TOPOLOGY: linear (xi) SEQUENCE DESCRIPTION: SEQ ID NO:3:

```
TCTAGACTCG AGCAGGGCAG ACTGGTAGCA AAGCCCCCAC GCCCAGCCAG GAGCACCGCC      60

GCGGACTCCA GCACACCGAG GGACATGCTG GGCCTGCGCC CCCCACTGCT CGCCCTGGTG     120

GGGCTGCTCT CCCTCGGGTG CGTCCTCTCT CAGGAGTGCA CGAAGTTCAA GGTCAGCAGC     180

TGCCGGGAAT GCATCGAGTC GGGGCCCGGC TGCACCTGGT GCCAGAAGCT GAACTTCACA     240

GGGCCGGGGG ATCCTGACTC CATTCGCTGC GACACCCGGC CACAGCTGCT CATGAGGGGC     300

TGTGCGGCTG ACGACATCAT GGACCCCACA AGCCTCGCTG AAACCCAGGA AGACCACAAT     360

GGGGGCCAGA AGCAGCTGTC CCCACAAAAA GTGACGCTTT ACCTGCGACC AGGCCAGGCA     420

GCAGCGTTCA ACGTGACCTT CCGGCGGGCC AAGGGCTACC CCATCGACCT GTACTATCTG     480

ATGGACCTCT CCTACTCCAT GCTTGATGAC CTCAGGAATG TCAAGAAGCT AGGTGGCGAC     540

CTGCTCCGGG CCCTCAACGA GATCACCGAG TCCGGCCGCA TTGGCTTCGG GTCCTTCGTG     600

GACAAGACCG TGCTGCCGTT CGTGAACACG CACCCTGATA AGCTGCGAAA CCCATGCCCC     660

AACAAGGAGA AAGAGTGCCA GCCCCCGTTT GCCTTCAGGC ACGTGCTGAA GCTGACCAAC     720

AACTCCAACC AGTTTCAGAC CGAGGTCGGG AAGCAGCTGA TTTCCGGAAA CCTGGATGCA     780

CCCGAGGGTG GGCTGGACGC CATGATGCAG GTCGCCGCCT GCCCGGAGGA AATCGGCTGG     840

CGCAACGTCA CGCGGCTGCT GGTGTTTGCC ACTGATGACG GCTTCCATTT CGCGGGCGAC     900

GGAAAGCTGG GCGCCATCCT GACCCCCAAC GACGGCCGCT GTCACCTGGA GGACAACTTG     960
```

```
TACAAGAGGA GCAACGAATT CGACTACCCA TCGGTGGGCC AGCTGGCGCA CAAGCTGGCT    1020

GAAAACAACA TCCAGCCCAT CTTCGCGGTG ACCAGTAGGA TGGTGAAGAC CTACGAGAAA    1080

CTCACCGAGA TCATCCCCAA GTCAGCCGTG GGGGAGCTGT CTGAGGACTC CAGCAATGTG    1140

GTCCATCTCA TTAAGAATGC TTACAATAAA CTCTCCTCCA GGGTCTTCCT GGATCACAAC    1200

GCCCTCCCCG ACACCCTGAA AGTCACCTAC GACTCCTTCT GCAGCAATGG AGTGACGCAC    1260

AGGAACCAGC CCAGAGGTGA CTGTGATGGC GTGCAGATCA ATGTCCCGAT CACCTTCCAG    1320

GTGAAGGTCA CGGCCACAGA GTGCATCCAG GAGCAGTCGT TTGTCATCCG GGCGCTGGGC    1380

TTCACGGACA TAGTGACCGT GCAGGTTCTT CCCCAGTGTG AGTGCCGGTG CCGGGACCAG    1440

AGCAGAGACC GCAGCCTCTG CCATGGCAAG GGCTTCTTGG AGTGCGGCAT CTGCAGGTGT    1500

GACACTGGCT ACATTGGGAA AAACTGTGAG TGCCAGACAC AGGGCCGGAG CAGCCAGGAG    1560

CTGGAAGGAA GCTGCCGGAA GGACAACAAC TCCATCATCT GCTCAGGGCT GGGGGACTGT    1620

GTCTGCGGGC AGTGCCTGTG CCACACCAGC GACGTCCCCG GCAAGCTGAT ATACGGGCAG    1680

TACTGCGAGT GTGACACCAT CAACTGTGAG CGCTACAACG GCCAGGTCTG CGGCGGCCCG    1740

GGGAGGGGGC TCTGCTTCTG CGGGAAGTGC CGCTGCCACC CGGGCTTTGA GGGCTCAGCG    1800

TGCCAGTGCG AGAGGACCAC TGAGGGCTGC CTGAACCCGC GGCGTGTTGA GTGTAGTGGT    1860

CGTGGCCGGT GCCGCTGCAA CGTATGCGAG TGCCATTCAG GCTACCAGCT GCCTCTGTGC    1920

CAGGAGTGCC CCGGCTGCCC CTCACCCTGT GGCAAGTACA TCTCCTGCGC CGAGTGCCTG    1980

AAGTTCGAAA AGGGCCCCTT TGGGAAGAAC TGCAGCGCGG CGTGTCCGGG CCTGCAGCTG    2040

TCGAACAACC CCGTGAAGGG CAGGACCTGC AAGGAGAGGG ACTCAGAGGG CTGCTGGGTG    2100

GCCTACACGC TGGAGCAGCA GGACGGGATG GACCGCTACC TCATCTATGT GGATGAGAGC    2160

CGAGAGTGTG TGGCAGGCCC CAACGATTTT TGGGTGCTGG TGGTGGTTGG TGGAGTCCTG    2220

GCTTGCTATA GCTTGCTAGT AACAGTGGCC TTTATTATTT TCTGGGTGAG GAGTAAGAGG    2280

AGCAGGCTCC TGCACAGTGA CTACATGAAC ATGACTCCCC GCCGCCCCGG GCCCACCCGC    2340

AAGCATTACC AGCCCTATGC CCCACCACGC GACTTCGCAG CCTATCGCTC CTGACACGGG    2400

TCGAC                                                                2405

(2) INFORMATION FOR SEQ ID NO:4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Lys Gly Ile Leu Gly Phe Val Phe Thr Leu Thr Val
1               5                   10
```

CHIMERIC RECEPTORS FOR THE GENERATION OF SELECTIVELY-ACTIVATABLE TH-INDEPENDENT CYTOTOXIC T CELLS

CROSS-REFERENCE TO RELATED APPLICATIONS

This application is the national phase of PCT/US95/14171, filed Nov. 1, 1995, designating the United States; which is a continuation of U.S. application Ser. No. 08/480,577, filed Jun. 7, 1995, now abandoned, which is a continuation-in-part of U.S. application Ser. No. 08/332,993, abandoned, filed Nov. 1, 1994.

TECHNICAL FIELD

The invention relates to the field of immunotherapy, more specifically to the introduction of genetic material encoding chimeric receptors into lymphocytes to generate cytotoxic T lymphocytes (CTLs) that are selectively-activatable and that have a lessened dependence on helper ($T_H$) cells and/or growth factors supplied by $T_H$ cells.

BACKGROUND

T lymphocytes are responsible primarily for protection against intracellular pathogens and malignancies. Individuals who are grossly deficient in T-cell immunity frequently succumb to overwhelming infections by organisms such as cytomegalovirus, Pneumocystis carinii, Candida, and other apparently opportunistic pathogens, including bacteria, viruses, and fungi. These individuals may also succumb to malignancies such as B cell lymphomas, indicating the importance of T cell immunity in the suppression or elimination of certain tumors. Immunosuppression can result from a variety of causes, including viral infections (for example, with the HIV virus), as a result of chemical therapy, and malignancies (particularly of type that affect the hematopoietic system).

Mature T lymphocytes generally express the CD3 cell surface molecule, but consist predominantly of two basic subtypes based on their mutually exclusive expression of cell surface molecules CD4 and CD8. Most CD4+ T cells are involved in "helper" functions in immune responses and secrete cytokine molecules, in particular interleukin 2 (IL-2), upon which the cytotoxic CD8+ T cells are dependent. Such CD4+ T cells are often referred to as T helper ($T_H$) cells. CD8+ cells are involved in "effector" functions in immune responses, such as direct cytotoxic destruction of target cells bearing foreign antigens, and represent an important mechanism for resistance to viral infections and tumors. The functional distinction between CD4+ and CD8+ T cells is based on the ability of CD4+ cells to recognize antigen presented in association with class II MHC molecules, and CD8+ cells to recognize antigen presented in association with class I MHC molecules. The CD8+ cells that mediate this lytic function are designated cytotoxic T lymphocytes (CTLs). Although most CTL are of the CD8+ phenotype, some CTL of the CD4+ phenotype have been described. Generally, individual CTLs (whether CD8+ or CD4+) are antigen-specific.

Lymphocytes are dependent upon a number of cytokines for proliferation. For example, CTLs are dependent on helper T ($T_H$) cell-derived cytokines, such as IL-2, for growth and proliferation in response to foreign antigens. (Zinkernagel and Doherty, *Adv. Immunol.* 27:51, 1979; Male et al., *Advanced Immunology*, Chap. 7, Gower Publ., London, 1987; Jacobson et al., *J. Immunol.* 133:754, 1984). IL-2, for example, is a potent mitogen for cytotoxic T lymphocytes (Gillis and Smith, *Nature* 268:154, 1977), and the combination of antigen and IL-2 causes proliferation of primary CD8+ T cells in vitro. The importance of IL-2 for the growth and maintenance of the CD8+ CTL in vivo has been documented in models of adoptive immunotherapy in which the therapeutic efficacy of transferred anti-retroviral CD8+ cells is enhanced by subsequent administration of IL-2 (Cheever et al., *J. Exp. Med.* 155:968, 1982; Reddehase et al., *J. Virol.* 61:3102, 1987). IL-4 and IL-7 are also capable of stimulating the proliferation of at least a subpopulation of mature CD8+ CTL (Alderson et al., *J. Exp. Med.* 172:577, 1990).

Considerable research has been focused on the use of T cells in treating malignant tumors and viral infections. Cytotoxic T cells specific for a particular type of tumor can be isolated and administered to a patient having a tumor with the effect that the CTLs ameliorate the tumor. It has been demonstrated, for example, that tumor-specific T cells can not only be generated to experimental tumors in mice but also that T cells with apparent tumor specificity can be isolated from human tumors. Such human tumor infiltrating lymphocytes (TILs) have been expanded in vitro and used to treat cancer patients, generating significant enthusiasm for human adoptive immunotherapy with tumor-specific T cells (Rosenberg et al., *N. Engl. Med.* 319:1767, 1988).

Similar studies using cytotoxic T cells specific for viral antigens have also been conducted in animal models. Human HIV-specific CTL of both the CD8+ (Walker et al., *Nature* 328:345, 1987; Plata et al., *Nature* 328:348, 1987) and CD4+ (Siliciano et al., *Cell* 54:561, 1988) phenotype have been isolated and characterized. HIV-specific CD8+ CTL are classical CTL in that their proliferative and cytotoxic responses are antigen-specific and MHC-restricted (Walker et al., supra; Chenciner et al., *Eur. J. Immuno.* 19:1537, 1989; Walker et al., *Proc. Natl. Acad. Sci. USA* 86:9514, 1989), in common with the numerous mouse and human CTL clones which have been characterized which are specific for viral, tumor or allospecific antigens.

The adoptive transfer of antigen (Ag)-specific T cells to establish immunity appears to be an effective therapy for some viral infections and tumors in the mouse animal model system (for a review see P. D. Greenberg, in *Advances in Immunology*, F. Dixon Ed. Academic Press, Inc. Orlando Fla. (1991), pp. 280–355). However, a successful outcome of an adoptive transfer method is dependent upon many factors, including the longevity of the transferred clones and the lack of toxicity to the host of the transferred cells. Although many antigen-specific T cell clones have been isolated, the use of tumor-specific T cell clones generated in vitro for tumor therapy has been shown to be subject to certain limitations. In particular, it has been demonstrated in several therapeutic models that the efficacy of cytolytic CD8+ T cells is limited by a dependency on exogenous IL-2 (produced by $T_H$ cells), a finding that has been substantiated in human adoptive therapy trials in which administration of exogenous IL-2 appears essential for optimal therapeutic efficacy (Rosenberg et al., *N. Engl. J. Med.* 319:1767, 1988; Klarnet et al., in Role of *Interleukin-2 Activated Killer Cells in Cancer*, Lutzova and Herberman (eds.), CRC Press, Florida, Chapter 14, pp. 199–218, 1990). Thus, while in vitro T cell cloning techniques provide a means to generate large numbers of T cells with demonstrable tumor or viral specificity, the full potential of using such antigen-specific T cells in therapy appears to be limited by their dependency on $T_H$ cells.

In some limited instances, the problem of $T_H$ dependency may be circumvented by using a particular class of CTLs that already function independently of $T_H$ cells. These cells are known as helper-independent cytolytic CD8+ cells (HIT$_c$) (Klarnet et al., *J. Immunol.* 142:2187, 1989) and have been identified in some populations of primary (i.e., freshly isolated from in vivo sources) CD8+ CTL (Sprent and Schaefer, *J. Exp. Med.* 162:21068, 1985; Andrus et al., *J. Exp. Med.* 159:647, 1984). HIT$_c$ cells produce sufficient IL-2 to grow independently of CD4+ cells and the cytokines they produce. HIT$_c$ cells have been shown to express plasma membrane IL-1 receptors (IL-1R) and require IL-1 for their IL-2-independent proliferation (Klarnet et al., 1989, supra). This is in contrast to conventional CD8+ CTL which do not express detectable IL-1R on their surface (Lowenthal and MacDonald, 1987). HIT$_c$ cells have been generated which are specific for a range of antigens, including tumor, viral and alloantigens (von Boehmer et al., *J. Immunol.* 133:59, 1984; Klarnet et al., *J. Immunol.* 138:4012, 1987; and Andrus et al., *J. Exp. Med.* 149:647, 1984; Mizouchi et al., *J. Immunol.* 142:270, 1989). HIT$_c$ specific for a retrovirally transformed tumor have been shown to eradicate the tumor cells and persist long-term in vivo following their engraftment (Klarnet et al., 1989, supra). However, analogous human HIT$_c$ cells having specificity for many important antigens, such as HIV, have not yet been isolated.

Another significant limitation is associated with the phenomenon of T cell activation. In particular, activation of CD8+ T cells requires the interaction of multiple receptor-ligand pairs. Engagement of the T cell receptor (TCR) by antigen-MHC is one required interaction. However, it alone does not induce T cell activation but rather energy. Thus, "second signals" are believed to be essential for T cell activation (see, e.g., Weiss and Imboden, *Adv. Immunol.* 41:198, 1987; Weaver and Unanue, *Immunol. Today,* 11:49, 1990). These second signals are believed to be provided by interactions between co-stimulatory molecules present on the T cell and cognate ligands present on the surface of the antigen presenting cell (APC).

However, not all cells that are capable of presenting antigen will also possess the appropriate cognate ligands for co-stimulation. As a result, T cell activation may fail to occur because potential APCs that are encountered by the T cell may lack appropriate ligands, and, conversely, APCs having the cognate ligand may be relatively restricted in occurrence.

Realizing the full potential of antigen-specific T cells in therapy would be facilitated by developing a more complete repertoire of lymphocytes, in particular, CTLs that can be more readily activated and that have a lessened dependency on $T_H$-cells. One approach, described by S. Lupton et al., has been to construct a hybrid gene comprising a region encoding a stimulatory factor polypeptide operably linked to a heterologous transcriptional control region, wherein the transcriptional control region causes activation-induced expression of the stimulatory factor encoding region when present in a lymphocyte that has been activated, and wherein expression of the stimulatory factor polypeptide in the activated lymphocyte reduces dependency of the lymphocyte on T helper cells ($T_H$ cells) (see U.S. Ser. No. 08/044,539, abandoned, filed 6 Apr. 1993; U.S. Ser. No. 08/244,448, U.S. Pat. No. 5,588,807, filed 6 Jun. 1994, and international counterpart PCT/US94/03679, filed 4 Apr. 1994). In that approach, activation of the lymphocyte results in coordinated expression of a stimulatory factor such as a cytokine.

In some situations, however, the lymphocytes may not be readily activatable. The present invention, described below, presents a different approach to the production of lymphocytes that are more readily activatable and that have a lessened dependency T helper cells.

SUMMARY OF THE INVENTION

The present invention provides vectors for producing lymphocytes that are, relative to the parental cells without the vector, more readily and/or selectively activatable and are capable of enhanced growth or proliferation in the presence of limiting amounts of $T_H$ cells or stimulatory factors (e.g. cytokines) provided by $T_H$ cells.

The vectors contain a recombinant gene, encoding a polypeptide that forms part of a chimeric receptor that is capable of enhancing growth or proliferation (once the receptor has engaged the appropriate ligand in conjunction with engagement of the TCR complex). The recombinant gene is controlled by a heterologous transcriptional control region which may be constitutively active or inducible in T cells.

The invention also provides lymphocytes containing the vectors and methods of using the vectors to create lymphocytes with that are selectively activatable and have a lessened dependency on $T_H$ cells and/or stimulatory factors they produce.

Thus, one embodiment of the invention is a recombinant polynucleotide comprising a domain encoding a receptor whose ligand is widely or selectively expressed fused to a signaling domain derived from the CD28 co-stimulatory receptor; which chimeric coding region is operably linked to a heterologous transcriptional control region. Another embodiment is a chimeric receptor protein encoded by such a recombinant polynucleotide. When expressed in a lymphocyte, binding of the ligand to the chimeric receptor results in activation of the CD28 co-stimulation pathway, leading to T cell activation and proliferation mediated by a self-stimulating "autocrine" growth cycle, as described below. Thus, signaling of the chimeric receptor, in conjunction with signaling by the TCR, causes activation of the lymphocyte and induces the production of stimulatory factors, thereby reducing the dependency of the CTL on $T_H$ cells.

Another embodiment of the invention is a host cell transformed with a recombinant polynucleotide as described above (and progeny thereof); wherein expression of the recombinant polynucleotide renders the T cell selectively activatable and reduces the dependency on $T_H$ cells.

Yet another embodiment of the invention is a method of using the above described polynucleotide comprising transforming a lymphocyte with the polynucleotide, wherein as a result of the transformation the lymphocyte is rendered selectively activatable and has a lessened dependency on $T_H$ cells for proliferation.

Another embodiment of the invention is a cell produced by the above-described method, and progeny thereof.

A number of preferred embodiments of the present invention are enumerated as follows:

1. A cytotoxic T lymphocyte (CTL) comprising a chimeric cell surface receptor, said chimeric receptor comprising a fusion polypeptide of the following structure:

XC—TM—IC28 wherein (XC) is an extracellular region derived from a receptor for a ligand (L) that is expressed on the surface of an antigen-displaying cell, fused via a transmembrane region (TM) to an intracellular region (IC28) which is derived from the intracellular region of the CD28 receptor. The CTLs of the present invention include both pre-CTLs and effector-CTLs; and these CTLs may be CD8 positive or CD4 positive. Derivatives of a naturally-occuring receptor include the corresponding region as well as conservative mutations thereof (e.g. substitutions, additions or deletions that do not substantially disrupt receptor binding/signalling).

2. A CTL of embodiment 1, wherein said CTL is selected from the group consisting of antigen-specific CD8 positive pre-CTLs and antigen-specific CD8 positive effector-CTLs. A sub-class of CTLs of the present invention are CD8 positive and recognize specific antigens displayed in association with Class I MHC, as described herein. By virtue of the chimeric receptors of the present invention, the novel CTLs described herein will be able to be interact with a wider variety of antigen-displaying cells (ADCs) than classical "antigen-presenting cells". In particular, since most nucleated cells can display antigen in association with the major histo-compatibility complex (MHC), most nucleated cells will be able to act as potential ADCs. It is also possible, however, to target the CTL containing the chimeric receptor to particular ADCs, as described below.

3. A CTL of embodiment 1, wherein both the transmembrane region (TM) and the intracellular region (IC28) are derived from the CD28 receptor. While the transmembrane region can be derived from any of a variety of sources (or synthetically designed), as is well known in the art, it is especially convenient to use the transmembrane region of the CD28 receptor (i.e. by simply utilizing a larger piece of CD28 that extends beyond IC28 to include the TM). In an illustrative embodiment, described below, base pairs +556 to +767 of the human CD28 gene (containing a TM and IC28) were prepared by PCR amplification from a human CD28 cDNA.

4. A CTL of embodiment 2, wherein L is a ligand that is generally expressed on human cells displaying antigens in association with class I MHC. A number of such widely expressed ligands are known in the art (see e.g. the references cited herein), and new cell surface ligands are regularly being identified. Many ligands that are involved in promoting adhesion are also widely-expressed. In illustrative embodiments below, an exemplary integrin (LFA-1) and a CD2 monomeric receptor are described which bind to the widely-expressed ligands ICAM-1 and LFA-3, respectively.

5. A CTL of embodiment 2, wherein L is a ligand that is expressed on a selected phenotypic subset of human cells displaying antigens in association with class I MHC. The receptor that is the source of XC can also be chosen to bind to a ligand that is selectively expressed, e.g., on a desired subset of cells, in a particular tissue, or at a particular developmental stage. A number of cell surface ligands that are differentially expressed have been described (see, e.g., the references cited herein).

6. A CTL of embodiment 2, wherein L is a ligand that mediates adhesion between a CTL and a human cell displaying antigen in association with class I MHC. Providing additional receptors for adhesion can enable or facilitate the process of T cell stimulation; or can be used to bind the T cells to particular desired target cells.

7. A CTL of embodiment 2, wherein XC is derived from the extracellular region of a monomeric receptor. Illustrative embodiments using both monomeric and oligomeric receptors are described below.

8. A CTL of embodiment 7, wherein said monomeric receptor is a CD2 cell surface molecule. In an illustrative embodiment using a monomeric receptor, the extracellular region of CD2 (base pairs 1–627) was amplified by PCR for use as a source of an XC region from a receptor with a widely-expressed cognate ligand.

9. A CTL of embodiment 2, wherein the chimeric receptor is a complex comprising at least two fusion polypeptides, each fusion polypeptide comprising an XC region derived from an individual polypeptide chain of an oligomeric receptor, fused via a TM region to an intracellular region derived from the CD28 receptor. Since hetero-oligomeric receptors comprise at least two different polypeptide chains that associate into a complex, the construction of chimeric receptors in which XC is derived from a hetero-oligomeric receptor will preferably involve recreating the native extracellular portion of the receptor by using XC regions derived from each of the different polypeptide chains. Illustrative embodiments of such constructions are the chimeric fusion peptides derived from LFA-1 and CD28 described below.

10. A CTL of embodiment 9, wherein said oligomeric receptor is a member of the integrin family of heterodimeric cell surface proteins.

11. A CTL of embodiment 10, wherein said oligomeric receptor is an LFA-1 cell surface molecule, and the chimeric receptor comprises two fusion polypeptides, one of which has an XC region derived from the alpha chain of LFA-1 and the other of which has an XC region derived from the beta chain of LFA-1. In illustrative embodiments described below, the human LFA-1 alpha and beta chains were obtained by PCR amplification from cDNAs (positions +1 to +3358 for the alpha chain, and positions +1 to +2072 for the beta chain).

12. A recombinant polynucleotide encoding a fusion polypeptide of the following structure:

XC—TM—IC28 wherein (XC) is an extracellular region derived from a receptor for a ligand (L) that is expressed on the surface of an antigen-displaying cell, fused via a transmembrane region (TM) to an intracellular region (IC28) which is derived from the intracellular region of the CD28 receptor.

13. A fusion polypeptide encoded by the recombinant polynucleotide of embodiment 12.

14. An expression vector comprising a promoter operably linked to the recombinant polynucleotide of embodiment 12. The vector can also contain, for example, a selectable marker.

15. An expression vector of embodiment 14, further comprising a bifunctional selectable fusion gene. In a particularly preferred embodiment, the vector contains a "bifunctional selectable fusion gene" (allowing for both positive and negative selection), as described by S. Lupton et al., see description and references below. An example of the use of such a bifunctional selectable fusion gene ("HyTK") is illustrated below.

16. A cell line producing viral particles that comprise an expression vector of embodiment 15. A variety of suitable vectors, including retroviral vectors, are described below and in the art. Another useful approach, involving non-viral gene delivery, has been described by R. Overell et al., see, U.S. Ser. No. 08/227,858, filed 15 Apr. 1994, and continuing application filed 19 Oct. 1994.

17. A method of using a recombinant polynucleotide of embodiment 12 to generate a selectively-activatable $T_H$-independent CTL, said method comprising the steps of: (a) providing a recipient CTL; and (b) transfecting said recipient cell with an expression vector comprising a promoter operably linked to a recombinant polynucleotide of embodiment 12, wherein expression of the recombinant polynucleotide in said recipient cell results in expression of a chimeric receptor at its cellular surface.

18. A method of embodiment 17, wherein said expression vector further comprises a bifunctional selectable fusion gene.

19. A selectively-activatable $T_H$-independent CTL produced by the method of embodiment 17 and progeny thereof.

20. A method of using a CTL of embodiment 1 to mediate lysis of a target cell bearing a cognate antigen, comprising allowing said CTL to come into contact with a target cell bearing a cognate antigen. The effector function of CTLs, i.e. target cell lysis, is well characterized in the art. CTLs of the present invention can be used to mediate lysis of antigen-displaying target cells either in vitro or in vivo.

BRIEF DESCRIPTION OF THE DRAWINGS

FIGS. 2A and 2B together present the nucleotide sequence (SEQ ID No:1) of the CD2/CD28 chimeric receptor. The sequence presented is the BamHI-SalI fragment inserted into the retroviral vector.

FIGS. 3A, 3B, 3C and 3D together present the nucleotide sequence (SEQ ID No: 2) of the LFA-1α/CD28 chimeric receptor. The sequence presented is the XbaI-KpnI fragment inserted into the retroviral vector.

FIGS. 4A, 4B, and 4C together present the nucleotide sequence (SEQ ID No: 3) of the LFA-1β/CD28 chimeric receptor. The sequence presented is the XbaI-SalI fragment inserted into the retroviral vector.

FIGS. 5A, 5B, and 5C together present the flow cytometry data demonstrating cell surface expression of the CD2/CD28 chimeric receptor on infected NIH 3T3 cells.

FIGS. 8A, 8B, 8C and 8D together present the flow cytometry data on the parental and transfected (A2 and B7-1) Jurkat cells.

FIGS. 9A, 9B, 9C and 9D together present the flow cytometry data on the parental and transfected (A2 and B7-1) HeLa cells.

DETAILED DESCRIPTION OF THE INVENTION

Figure 1:
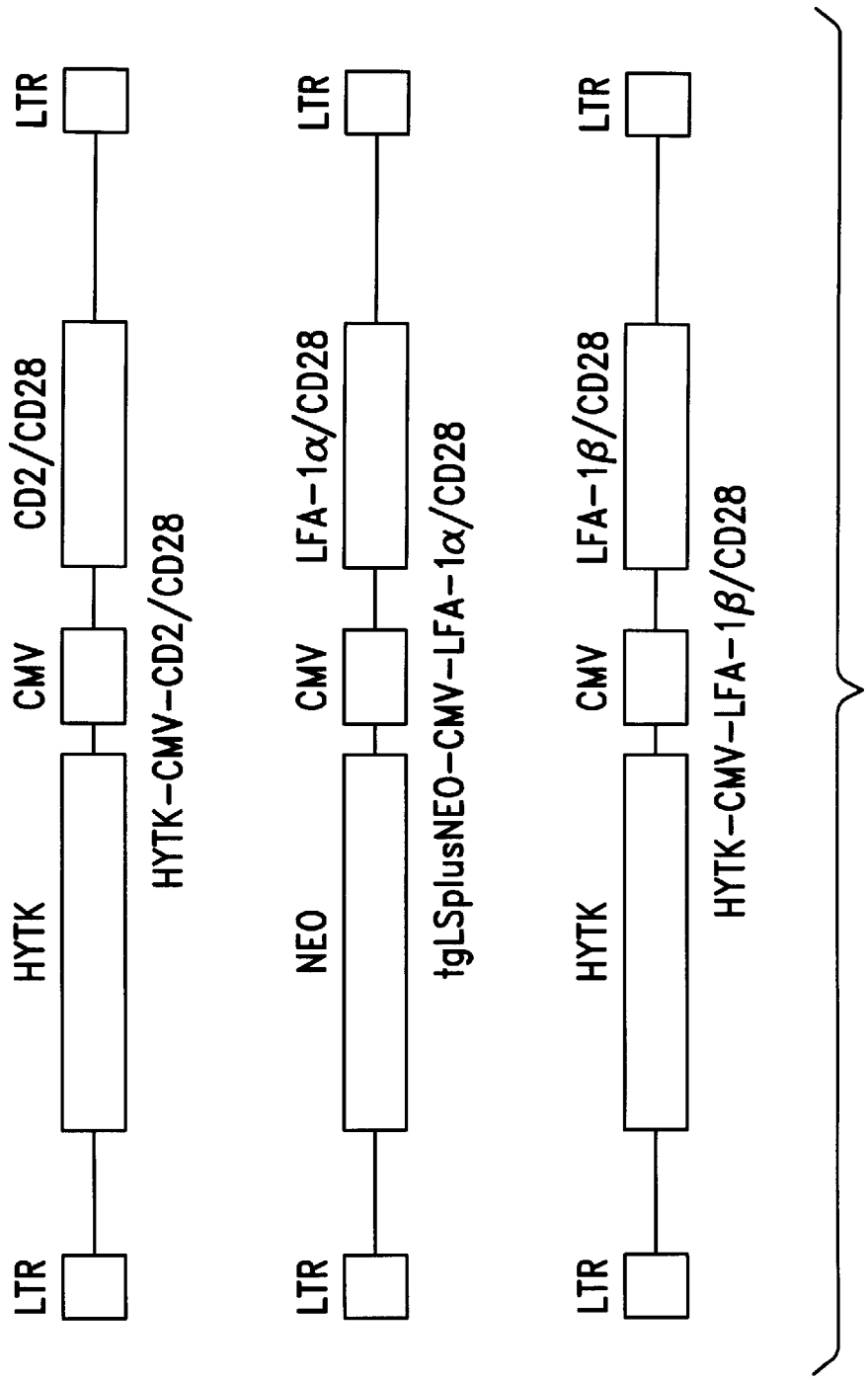
FIG. 1 presents schematic illustrations of the proviral structures of the retroviral vectors named HyTK-CMV-CD2/CD28, tgLSplusNEO-CMV-LFA1α/CD28, and HyTK-CMV-LFA1β/CD28.
Figure 5B:
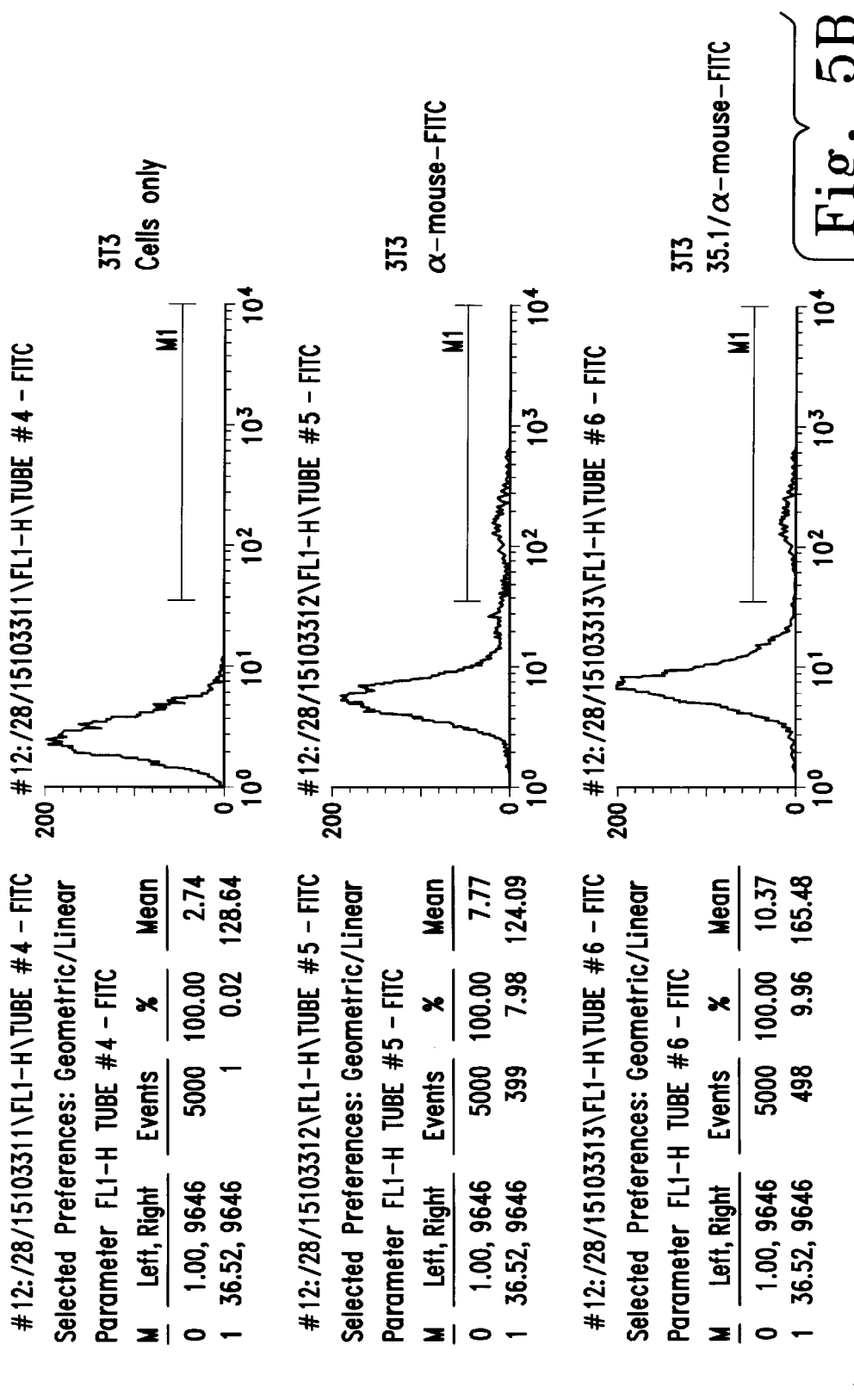
Figure 6:
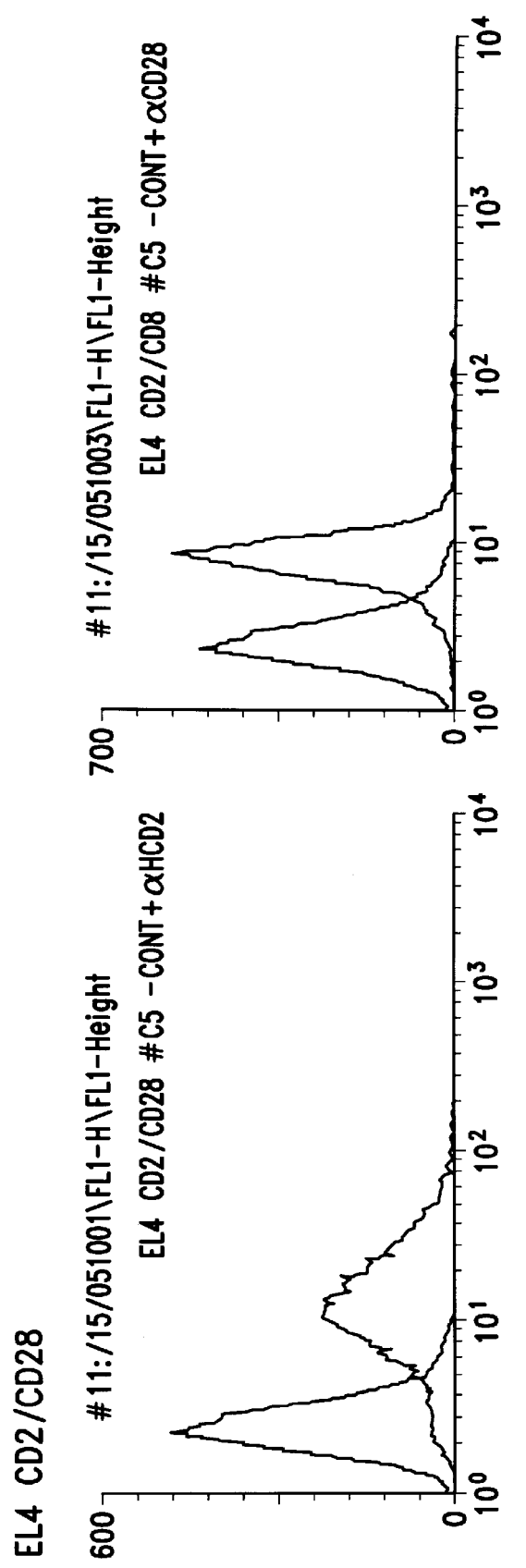
FIG. 6 presents the flow cytometry data demonstrating cell surface expression of the CD2/CD28 chimeric receptor on transfected EL-4 (clone 5) cells.

The invention provides T lymphocytes that differ from the parental lymphocytes by the presence of a recombinant polynucleotide that encodes a chimeric receptor. The chimeric receptor enables the lymphocyte to become activated and to proliferate (via a $T_H$-independent autocrine cycle) in response to adhesion between the lymphocyte and an antigen displaying cell (ADC) that might not normally activate the T cell.

As described in more detail below, the chimeric receptors of the present invention comprise fusion polypeptides of the following type:

XC—TM—IC28 wherein (XC) is an extracellular region derived from a receptor (R) for ligand (L), fused via a transmembrane region (TM) to an intracellular region (IC28) which is derived from the intracellular domain of the CD28 receptor.

The particular usefulness of the chimeric receptors of the present invention is believed to arise from the involvement of CD28 in a process referred to as "co-stimulation". It has been observed that the activation of CD8+ T cells requires the interaction of multiple receptor-ligand pairs. Engagement of the T cell receptor (TCR) by antigen/MHC bound to the surface of an antigen presenting cell is one required interaction, but it alone does not induce T cell activation. On the contrary, interaction of the TCR and antigen/MHC, without interaction of other receptor-ligand pairs can result in functional inactivation or "anergy". These other interactions have been described as providing "second signals" which are required for T cell activation (see, e.g., Weiss and Imboden, *Adv. Immunol.* 41:198, 1987; Weaver and Unanue, *Immunol. Today,* 11:49, 1990). These second signals are believed to be provided by interactions between co-stimulatory molecules present on the T cell and cognate ligands present on the surface of the antigen presenting cell (APC).

Several T cell adhesion receptors have been described. Although most of these receptors (e.g. CD2, LFA-1) augment TCR-mediated signals which can lead to T cell activation, it is believed that these receptors provide only minimal co-stimulatory signals and that their role in T cell activation primarily involves increasing the avidity between the T cell and the APC (Jenkins and Johnson, *Current Opinion In Immunol.* 5:361, 1993). Evidence indicates that CD28, however, provides a co-stimulatory signal which is distinct from the pathway initiated by the TCR (see, e.g., P. Stein et al., *Molecular and Cellular Biology,* 1994, 14:3392–3402, and references cited therein).

The CD28 receptor, a cell surface glycoprotein which is part of the Ig superfamily, is composed of two identical disulfide linked 44 kDa subunits. CD28 is expressed on all CD4+ T cells and about 50% of human CD8+ T cells. Engagement of both the TCR and CD28 (with each of their corresponding ligands) results in T cell activation and proliferation. Such proliferation is generally mediated by a self-stimulating (and thus, $T_H$-independent) cycle known as an "autocrine" growth cycle involving enhanced expression of a number of cytokines including IL-2, IFNγ, GM-CSF, and TNFα (June et al., *Immunol. Today* 11:211, 1990; Allison, *Current Opinion in Immunol.* 6:414, 1994). Recent studies have demonstrated that the increase in cytokine production is due to increased transcription rates in addition to stabilization of the mRNAs. Activation can also result in the increased expression of cell surface receptors for one or more of the autocrine growth factors, thereby further enhancing the proliferative response. As a result, the activated CTLs become substantially less dependent on T helper cells for the provision of growth factors. Stimulation via the CD28 pathway alone does not appear to induce cytokine production or proliferation of T cells. Rather, CD28 signals appear to augment those delivered by the interaction of the TCR:CD3 complex with antigen:MHC; or by, e.g., phorbol ester treatment.

The belief that the CD28 signaling pathway is distinct from the TCR pathway is based in part on observations that cyclosporin A can significantly inhibit TCR-mediated stimulation; but, after TCR stimulation, co-stimulation via CD28 is completely resistant to the inhibitory effects of cyclosporine A.

Co-stimulation via the CD28 pathway is thus believed to be important for enabling and/or enhancing the activation of T lymphocytes. There are, however, significant practical limitations associated with CD28 stimulation. In particular, while two cognate ligands for CD28 have been identified, named "B7-1" and "B7-2", the expression of the B7 ligands is fairly restricted. Thus, expression of B7-1 is believed to be restricted to activated B cells, dendritic cells and monocytes (Vandenberghe et al., *Int. Immunol.* 5:317, 1993); and expression of B7-2 is apparently limited to resting B cells, dendritic cells and monocytes (Azuma et al., *Nature* 366:76, 1994; Freeman et al., *Science* 262:909, 1994).

In order to overcome these obstacles and to take full advantage of the CD28 co-stimulation pathway, the present invention effectively de-constructs the CD28 co-stimulation pathway and rebuilds it in a manner that allows the pathway to be activated by a wider range of ligands.

The chimeric receptors of the present invention function by uncoupling CD28 signal transduction from its normal dependence on ligands that are subject to restricted expression; and coupling it instead to another selected ligand including, for example, a very widely-expressed ligand; or a ligand that is selectively expressed in a desired target population of cells (such as those making up a particular tissue). Thus, in lymphocytes containing the chimeric receptors, CD28 signal transduction and concomitant activation and proliferation are driven by ligands other than those normally required for CD28 stimulation. As a result, T cell activation and proliferation can be broadened or selectively targeted.

The selected ligand can also provide a desired "accessory activity" such as promoting adhesion between the T cell bearing the chimeric receptor and the antigen displaying cell bearing the ligand, as described below. By selecting an adhesion molecule that is selectively expressed, the chimeric receptor can be used to effectively direct the host CTL to a particular target population.

In one preferred embodiment of the present invention, ligand L is a cell surface ligand that is widely expressed on the surface of cells that are displaying non-autologous antigens such as viral or tumor antigens. In another preferred embodiment of the present invention, ligand L is a cell surface ligand that is expressed on the surface of a selected subset of antigen displaying cells (ADCs). Since the chimeric receptors of the present invention can be designed to promote selective adhesion and/or selective stimulation of the host CTL, they can also be used to effectively direct the lymphocytes to a selected target population, such as an organ that is affected by a particular tumor or virus.

The extracellular region (XC) will be derived from that portion of receptor (R) that is known or determined to be located outside of the cellular membrane and that is believed to comprise a domain that binds ligand L.

The transmembrane region (TM) is preferably a portion of a membrane-bound polypeptide that is known or believed to span the cellular membrane, thereby anchoring the remainder of the polypeptide. In the chimeric constructs of the present invention, TM is conveniently (and preferably) derived from the transmembrane region of the CD28 receptor or that of the receptor (R). In our preferred embodiments, it is derived from the CD28 receptor. However, other peptides having characteristic transmembrane anchoring regions can be used as the source of TM, or a synthetic TM can be prepared.

As discussed below, the chimeric receptor may comprise one or more fusion peptide chains. That is, the chimeric receptor may be a monomeric receptor or an oligomeric receptor; depending on whether the XC source receptor (R) is a monomeric receptor or an oligomeric receptor. Most conveniently, the chimeric receptor is a monomeric receptor.

Binding of the ligand L to the chimeric receptor (via the extracellular region XC) delivers the proliferative signal normally associated with binding of a CD28 ligand to the CD28 receptor. An illustrative example of a monomeric receptor, described below, involves chimeric receptors in which region XC is derived from the intercellular adhesion molecule CD2, the corresponding ligand of which (LFA-3) is expressed on the surface of a wide variety of hematopoietic and nonhematopoietic cells. An illustrative example of a multimeric receptor, also described below, involves chimeric receptor proteins in which the multiple XC regions are derived from the intercellular adhesion molecule LFA-1, the corresponding ligand of which (ICAM-1) is also widely expressed on hematopoietic and nonhematopoietic cells. As described below, cytotoxic T lymphocytes containing such chimeric CD2/CD28 or LFA-1/CD28 receptors exhibit CD28-like co-stimulatory responses under conditions of limiting levels of the normal ligands for CD28 (the B7 ligands which are typically present at limiting levels).

Suitable sources of the XC region are receptors for which the cognate ligand L is present at non-limiting levels in the environment in which it is desired that the lymphocytes are activated. A preferred class of such ligands are those involved in T cell adhesion and/or co-stimulation. Among such ligands, especially preferred examples include CD44 and members of the integrin family. The most conveniently used receptors within these groups are those which are monomeric. A "targeting" chimeric receptor can also be designed, using a receptor (R) that is generally expressed on cells within a particular desired sub-population such as an organ. Examples of suitable receptors would be those that interact with adhesion ligands present on the desired target population. A large number of such cognate receptor-ligand pairs are known in the art; see, e.g., the review by Collins et al., *Current Opinions in Immunology* 6:385, 1994.

In a preferred embodiment of the present invention, the extracellular region (XC) is derived from a receptor that binds to a ligand found on an antigen displaying cell (ADC). The following points should be noted, however.

First, although stimulation of the CTL via both the TCR pathway and the CD28 co-stimulation pathway is believed to be required for optimal activation and concomitant proliferation (via the $T_H$-independent autocrine cycle), the two pathways need not be stimulated by a single antigen displaying cell. For example, an ADC might provide TCR-mediated stimulation, and CD28-mediated stimulation might come from a third cell that is displaying ligand L. It is also possible to trigger CD28-mediated stimulation (via the chimeric receptor) using a "free ligand" that is not bound to an ADC. Thus, for example, XC can be derived from a cytokine receptor, or another receptor for a ligand that is not bound to a cellular surface. Such a free ligand can be one that is naturally occurring in the body or a portion thereof; or it can be a ligand that is to be furnished as part of a therapeutic regimen.

Second, it should be emphasized that antigen displaying cells (ADCs) are not limited to classical antigen presenting cells (APCs). On the contrary, since most nucleated cells can display antigen in association with the major histocompatibility complex (MHC), most nucleated cells will be able to act as potential ADCs. Of course, as described herein, it will also be possible to target the host CTL containing the chimeric receptor to particular ADCs, if desired. For example, region XC can be derived from a receptor that selectively binds to an adhesion ligand on the surface of the target ADC.

Definitions

The following definitions are intended to supplement the detailed description of the invention.

The "major histocompatibility complex" (or "MHC") is a region of highly polymorphic genes encoding proteins that are expressed on the surface of a wide variety of cells; including for example, the human MHC loci (also known as "HLA" loci), and the murine MHC loci (also known as "H2" loci). "MHC" is also used to refer to the encoded proteins.

"Lymphocytes" as used herein, are cells that specifically recognize and respond to non-self antigens, and are responsible for development of specific immunity. Included within "lymphocytes" are B-lymphocytes and T-lymphocytes of various classes.

"Cytotoxic T lymphocytes" or "CTLs" are T cells which bear the CD3 cell surface determinant and which form the phylogenetic family of lymphocytes that are involved in the cell-mediated lysis of target cells bearing cognate antigens. CTLs include pre-CTLs and effector CTLs. "Pre-CTLs" are virgin or memory T lymphocytes that are committed to proliferating towards or being activated into effector-CTLs upon stimulation by antigen-displaying cells and/or accessory cells. "Effector CTLs" arise from the activation of pre-CTLs, and respond to antigen-bearing target cells by mediating lysis of the target cell. Most CTLs are of the CD8+ phenotype, but some CTLs are CD4+. CTLs are generally antigen-specific and MHC-restricted in that they recognize antigenic peptides only in association with the Major Histocompatibility Complex (MHC) molecules on the surface of target cells. CTLs may be specific for a wide range of viral, tumor or allospecific antigens, including HIV, EBV, CMV and a wide range of tumor antigens. Some CTLs, however, may not be antigen specific, for example, some cloned CTLs can be induced to lose some of their specificity for their cognate antigen by culture in abnormally high concentrations of IL-2 (Brooks et al., *Immunol. Rev.* 72:43, 1983). An especially preferred method for culturing CTLs in vitro is the "Rapid Expansion Method (REM)" described by Stanley Riddell in U.S. Pat. application Ser. No. 08/299,930, abandoned, filed Aug. 31, 1994, and continuation application Ser. No. 08/317,100, U.S. Pat. No. 5,827,642, filed Oct. 3, 1994 (incorporated herein by reference).

"Helper T cells" or "helper cells" or "$T_H$-cells" are a functional subclass of T cells which can help to generate cytotoxic T cells and cooperate with B cells in the production of an antibody response. Helper cells usually recognize antigen in association with class II MHC molecules.

An "antigen displaying cell" or "ADC", as used herein, refers to a cell that expresses an MHC-associated antigen on its surface that can be recognized by a T lymphocyte of the present invention. Since the present invention effectively allows the T lymphocyte to be activated by a broader range of antigen displaying cells (by virtue of their modified CD28 co-stimulation pathway), the pool of potential ADCs is effectively expanded beyond the "classical APCs" that are normally capable of activating T lymphocytes. Using the lymphocytes of the present invention, the ADC pool is thus expanded to include many other cells that display MHC-associated antigen. In a preferred embodiment of the present invention, the ADC will also express a ligand that is capable of interacting with the chimeric receptors on the lymphocytes. In other embodiments of the present invention, the ligand capable of binding to the chimeric receptor may be expressed on a third cell; or may be a "free" ligand that is not bound to a cellular surface, such as a cytokine.

An "antigen specific T cell clone" is comprised of the progeny of a single cell; the cells in this type of clone are of the same phenotype and are all targeted towards the same antigen. Methods of preparing antigen-specific T cell clones are known in the art. A preferred method of culturing antigen-specific T cell clones in vitro is the "Rapid Expansion Method" described by S. Riddell et al., supra.

"Antigen specific expression" refers to expression that occurs when the T cell recognizes its cognate antigen.

"Cognate antigen" refers to antigen, a peptide of which is associated with an MHC molecule, such that it forms a ligand that binds to a lymphocyte that recognizes it and causes triggering of signals for the effector function of the cell and/or for proliferation.

A CTL is "cytolytically specific for" cells expressing tumor or viral antigens if the CTL is capable of selectively recognizing and lysing the cells bearing the tumor or viral antigen. A CTL is "cytolytically reactive against" cells expressing tumor or viral antigens if the CTL is capable of lysing the cells bearing the tumor or viral antigen.

An "activated lymphocyte" is one that as a result of binding of a cognate antigen is producing polypeptide factors (including, for example, cytokines) at a level that is elevated relative to the lymphocyte without the bound cognate antigen.

A "selectively-activatable $T_H$-independent" CTL is, relative to the CTL from which it was derived, capable of activation by a selected range of antigen displaying cells and exhibits enhanced growth or proliferation in the presence of limiting quantities of CD4+ T helper ($T_H$) cells and/or a cytokine normally required for proliferation or growth. Growth or proliferation can be measured, for example, by any in vitro proliferation or growth assay or by any assay measuring the ability of the CTLs to persist in vivo. CTLs capable of enhanced growth or viability may have an augmented ability to destroy target cells bearing foreign antigens or to provide long-term immunologic memory.

"Cytokine" refers to a polypeptide that is a soluble intercellular signalling molecule, including for example, the interleukins, interferons, colony stimulating factors and TNFs.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as the modifications known in the art, both naturally occurring and non-naturally occurring.

"Transfection" or "transformation", as used herein, refer to the insertion of an exogenous polynucleotide into a host cell, irrespective of the method used for the insertion, including for example, viral-mediated transfer, as well as electroporation and other methods of direct uptake. The exogenous polynucleotide may be maintained as a non-integrated vector, for example, a plasmid, or alternatively, may be integrated into the host cell genome.

The term "recombinant expression vector" refers to a replicable unit of DNA or RNA in a form which is capable of being introduced into a target cell by transformation, electroporation, transduction or viral infection, and which codes for the expression of a heterologous structural coding sequence, for example, a cytokine, which is transcribed into mRNA and translated into protein under the control of elements having a regulatory role in gene expression. Such vectors will preferably also contain appropriate transcription and translation initiation and termination sequences.

"Recombinant," as used herein, means that a particular DNA sequence is the product of various combinations of cloning, restriction, and ligation steps resulting in a construct having a structural coding sequence distinguishable from homologous sequences found in natural systems. Generally, DNA sequences encoding the structural coding sequence, for example receptors, can be assembled from cDNA fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where such sequences do not interfere with manipulation or expression of the coding regions.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

A "transcriptional regulatory region" encompasses all the elements necessary for transcription, and may include elements necessary for regulation. Thus, a transcriptional regulatory region includes at least the promoter sequence, and may also include other regulatory sequences such as enhancers, and transcription factor binding sites.

"Operably linked" refers to a juxtaposition wherein the components so described are in a relationship permitting hem to function in their intended manner. For instance, a promoter is operably linked to a coding sequence if the promoter affects its transcription or expression.

"Treatment" as used herein refers to prophylaxis and/or therapy.

An "individual" as used herein refers to vertebrates, particularly members of the mammalian species, and includes but is not limited to domestic animals, sports animals, and primates, including humans.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

Illustrations of Certain Embodiments

By way of illustration, one chimeric receptor of the present invention consists of an extracellular region (XC) derived from the CD2 receptor; fused via a transmembrane region (TM), to an intracellular region (IC28), with both the TM and IC28 regions being derived from the CD28 receptor. The extracellular region of this chimeric receptor would bind to the ligand for CD2 (i.e. LFA-3); but the intracellular region of the chimeric receptor would transmit the proliferative signal of CD28. Full activation and proliferation of the cells occurs when the extracellular domain of the chimeric receptor binds to its cognate ligand and the TCR:CD3 complex binds to antigen:MHC (or is otherwise stimulated).

Oligomeric chimeras of the present invention are proteins comprising multiple polypeptide chains each having cytoplasmic domains derived from CD28 (more preferably both cytoplasmic and transmembrane domains are derived from CD28), and extracellular domains that are derived from polypeptide chains that normally form an oligomeric receptor. The design of some of the chimeric receptors of the present invention is illustrated as follows.

As a first illustration of the present invention, the CD2 protein was selected as the source of the extracellular region of a monomeric chimeric receptor. Factors influencing the selection of CD2 as a preferred illustration of a monomeric chimera included the fact that it has a widely expressed ligand, and secondarily that is believed to be an "accessory molecule" in T cell activation/interaction. A variety of such preferred accessory molecules are known and many more are being identified; see, e.g., Abbas, A. K. et al., *Cellular and Molecular Immunology* (W. B. Saunders, 1991, 1994); see also, for example, the monographs in the Annual Review of Immunology, Advances in Immunology, and the Journal of Experimental Medicine.

The CD2 protein (also known as T11, LFA-2, Leu-5 and Tp50) is a glycoprotein of about 45–50 kd and is generally present on at least about 90% of mature T lymphocytes. The molecule contains two extracellular globular domains that appear to be related to immunoglobulin ("Ig") homology units present in proteins of the Ig superfamily. It is believed that one role of CD2 in T cell activation/interaction is to promote intercellular adhesion.

An identified ligand for CD2 is the structurally similar molecule leukocyte function-associated antigen-3 (LFA-3, CD58). LFA-3 is a surface glycoprotein of about 55–70 kd and is expressed on a wide variety of hematopoietic and nonhematopoietic cells. The extracellular domain structure of LFA-3 is similar to that of CD2 and the binding of LFA-3 to CD2 promotes cell-to-cell adhesion.

The structure of the CD2 protein and the coding sequences of the CD2 gene have been described; see, e.g., Seed & Aruffo, *Proc. Natl. Acad. Sci. USA* 84:3365–3369, 1987. The extracellular region of CD2, which is about 190 amino acid residues in length, is followed by a hydrophobic transmembrane region of about 26 amino acid residues, and a cytoplasmic region of about 116 amino acid residues.

The construction of a monomeric chimera of the present invention, derived from CD2 and CD28, is illustrated below. Demonstrations of the functionality and utility of the CD2/CD28 chimeric receptor are also described below.

As another illustration of the present invention, the LFA-1 protein was selected as the source of the extracellular region for construction of a hetero-oligomeric chimera. Factors influencing the selection of LFA-1 as an illustration of a hetero-oligomeric chimera included the fact that it has a widely expressed ligand, and secondarily that is a member of the "integrin" family of proteins.

The LFA-1 protein (CD11aCD18) is also an intercellular adhesion molecule, and is expressed on virtually all bone marrow-derived cells, including more than 90% of mature T cells. LFA-1 is a member of the "integrin" family of proteins which are heterodimeric cell surface proteins composed of two noncovalently linked polypeptide chains, $\alpha$ and $\beta$. The extracellular domains of the two chains forming the proteins in the integrin family bind to various ligands, including extracellular matrix glycoproteins, complement components, and proteins on the surface of other cells.

An identified ligand for LFA-1 is intercellular dhesion molecule-1 (ICAM-1, CD54), an 80–114 kd integral membrane glycoprotein that is a member of the Ig superfamily, containing five extracellular Ig-like domains. ICAM-1 is expressed on a wide variety of hematopoietic and nonhematopoietic cells, including B and T cells, fibroblasts, keratinocytes, and endothelial cells.

The structure of the LFA-1 polypeptide chains and the coding sequences of the LFA-1 $\alpha$ and $\beta$ genes have been described by Larson et al., *J. Cell. Biol.* 108:703, 1989; and Kishimoto et al., *Cell* 48:681, 1987; respectively. The extracellular region of LFA-1$\alpha$, which is about 1063 amino acid residues in length, is followed by a hydrophobic transmembrane region of about 29 amino acid residues, and a cytoplasmic region of about 53 amino acid residues.

The extracellular region of LFA-1$\beta$, which is about 677 amino acid residues in length, is followed by a hydrophobic transmembrane region of about 23 amino acid residues, and a cytoplasmic region of about 46 amino acid residues.

The chimeric receptors may be constructed from cDNAs encoding the desired segments, although other methods are readily apparent to those of ordinary skill in the art. In one method, for example, the chimeric receptor DNA is prepared by providing cloned cDNAs encoding the upstream extracellular region from a selected receptor and the downstream CD28 transmembrane and cytoplasmic domains. These cloned cDNAs, if prepared by restriction enzyme digestion, may contain unwanted sequences that would intervene in the fusion. The unwanted sequences are removable by techniques known to those of ordinary skill in the art, including loop-out site-directed mutagenesis or splice-overlap extension polymerase chain reaction (PCR). The sequence of the chimeric cDNA encoding the receptor may then be confirmed by standard DNA sequencing methods. Specific examples of such chimeric receptors are illustrated in more detail below.

The polynucleotide regions encoding the chimeric receptors are generally operably linked to control regions that allow expression of the chimeric receptor in a host cell, particularly a CTL. Control regions include, at least, a promoter and a ribosomal binding site, and may also include, inter alia, enhancer regions, splice regions, polyadenylation regions, transcription and/or translation termination regions, and transcription and/or translation factor binding sites. These control regions may be present in recombinant vectors, particularly in recombinant expression vectors.

The ability of the chimeric receptor to enhance activation and proliferation of the host CTL is readily demonstrated by techniques known in the art. For example, cell lines that express the chimeric receptors can be stimulated via the TCR and the chimeric CD28 pathways by providing, respectively, any of a variety of means for stimulating the TCR, and the ligand corresponding to the chimeric CD28 receptor (whether cell-bound or free); and then tested for activation and proliferation in the absence of cytokines that are normally required for growth of the CTL.

The invention contemplates transforming lymphocytes with at least one type of chimeric receptor to allow the cells to be activated by a different range of ADCs and, consequently, to lessen the dependence upon at least one cytokine or other growth factor produced by $T_H$ cells. However, it is also within the invention to transform lymphocytes with multiple forms of chimeric receptors.

Techniques for nucleic acid manipulation are described generally, for example, in Sambrook et al. (1989), supra., Ausubel et al. (1987), supra. and in *Annual Reviews of Biochemistry* (1992) 61:131–156. Reagents useful in applying such techniques, such as restriction enzymes and the like, are widely known in the art and commercially available from a number of vendors.

Large amounts of the polynucleotides used to create the cells of the present invention may be produced by replication in a suitable host cell. The natural or synthetic polynucleotide fragments coding for a desired fragment may be incorporated into recombinant nucleic acid constructs, typically polynucleotide constructs, capable of introduction into and replication in a prokaryotic or eukaryotic cell. Usually the constructs will be suitable for replication in a unicellular host, such as yeast or bacteria, but may also be intended for introduction to, with and without and integration within the genome, cultured mammalian or plant or other eukaryotic cell lines. Purification of nucleic acids produced by the methods of the present invention can be achieved by methods known in the art and described, e.g., in Sambrook et al. (1989) and Ausubel et al. (1987). Of course, the polynucleotides used in the present invention may also be produced in part or in total by chemical synthesis, e.g., by the phosphoramidite method described by Beaucage and Carruthers (1981) *Tetra. Letts.* 22:1859–1862 or the triester method according to Matteucci et al. (1981) *J. Am. Chem. Soc.* 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host cell for replication will typically comprise a replication system recognized by the host, including the intended recombinant polynucleotide fragment encoding the desired polypeptide. Such vectors may be prepared by means of standard recombinant techniques well known in the art and discussed, for example, in Sambrook et al. (1989) or Ausubel et al.

Preferably, the polynucleotide construct will contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for *Bacilli*. The choice of the proper selectable marker will depend on the host cell, and appropriate markers for different hosts are well known in the art.

The polynucleotides of the present invention may be introduced into the desired T cell by any of a variety of means known in the art, including, for example, transformation, electroporation, lipofection, and transduction, including the use of viral vectors, which are currently a preferred means of introduction, as described below.

Various infection techniques have been developed which utilize recombinant infectious virus particles for gene delivery. This represents a preferred approach to the present invention. The viral vectors which have been used in this way include virus vectors derived from simian virus 40 (SV40) (Karlsson et al., *Proc. Natl. Acad. Sci. USA* 84 82:158, 1985); adenoviruses (Karlsson et al., *EMBO J.* 5:2377, 1986); adeno-associated virus (AAV) (B. J. Carter, *Current Opinion in Biotechnology* 1992, 3:533–539; and Flotte et al., U.S. Pat. application Ser. No. 08/149,332, abandoned, filed 9 Nov. 1993); and retroviruses (*Coffin*, 1985, pp. 17–71 in Weiss et al. (eds.), RNA Tumor Viruses, 2nd ed., Vol. 2, Cold Spring Harbor Laboratory, New York). Thus, gene transfer and expression methods are numerous but essentially function to introduce and express genetic material in mammalian cells. Several of the above techniques have been used to transduce hematopoietic or lymphoid cells, including calcium phosphate transfection (Berman et al., supra, 1984), protoplast fusion (Deans et al., supra, 1984), electroporation (Cann et al., *Oncogene* 3:123, 1988), and infection with recombinant adenovirus (Karlsson et al., supra; Reuther et al., *Mol. Cell. Biol.* 6:123, 1986), adeno-associated virus (LaFace et al., supra) and retrovirus vectors (Overell et al., *Oncogene* 4:1425, 1989). Primary T lymphocytes have been successfully transduced by electroporation (Cann et al., supra, 1988) and by retroviral infection (Nishihara et al., *Cancer Res.* 48:4730, 1988; Kasid et al., supra, 1990; and Riddell, S. et al., *Human Gene Therapy* 3:319–338, 1992).

Retroviral vectors provide a highly efficient method for gene transfer into eukaryotic cells and retroviral transfer is the currently preferred method for the delivery of the polynucleotides of the invention into CTLs. Among other things, retroviral integration tends to take place in a controlled fashion and results in the stable integration of one or a few copies of the new genetic information per cell.

Retroviruses are a class of viruses which replicate using a virus-encoded, RNA-directed DNA polymerase, or reverse transcriptase, to replicate a viral RNA genome to provide a double-stranded DNA intermediate which is incorporated into chromosomal DNA of an avian or mammalian host cell. Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. A characteristic feature of retroviral genomes (and retroviral vectors used as described herein) is the retroviral long terminal repeat, or LTR, which is an untranslated region of about 600 base pairs found in slightly variant forms at the 5' and 3' ends of the retroviral genome. When incorporated into DNA as a provirus, the retroviral LTR includes a short direct repeat sequence at each end and signals for initiation of transcription by RNA polymerase II and 3' cleavage and polyadenylation of RNA transcripts. The LTR contains all other cis-acting sequences necessary for viral replication.

A "provirus" refers to the DNA reverse transcript of a retrovirus which is stably integrated into chromosomal DNA in a suitable host cell, or a cloned copy thereof, or a cloned copy of nonintegrated intermediate forms of retroviral DNA. Forward transcription of the provirus and assembly into infectious virus occurs in the presence of an appropriate helper virus or in a cell line containing appropriate sequences enabling encapsidation without coincident production of a contaminating helper virus. Mann et al. (*Cell* 33:153, 1983) describe the development of cell lines (e.g., ψ2) which can be used to produce helper-free stocks of recombinant retrovirus. These cells lines contain integrated retroviral genomes which lack sequences required in cis for encapsidation, but which provide all necessary gene product in trans to produce intact virions. The RNA transcribed from the integrated mutant provirus cannot itself be packaged, but these cells can encapsidate RNA transcribed from a recombinant retrovirus introduced into the same cell. The resulting virus particles are infectious, but replication-defective, rendering them useful vectors which are unable to produce infectious virus following introduction into a cell lacking the complementary genetic information enabling encapsidation. Encapsidation in a cell line harboring trans-acting elements encoding an ecotropic viral envelope (e.g., ψ2) provides ecotropic (limited host range) progeny virus. Alternatively, assembly in a cell line containing amphotropic packaging genes (e.g., PA317, ATCC CRL 9078; Miller and Buttimore, *Mol. Cell. Biol.* 6:2895, 1986) provides amphitropic (broad host range) progeny virus. Such packing cell lines provide the necessary retroviral gag, pol and env proteins in trans. This strategy results in the production of retroviral particles which are highly infectious for mammalian cells, while being incapable of further replication after they have integrated into the genome of the target cell. The product of the env gene is responsible for the binding of the retrovirus to viral receptors on the surface of the target cell and therefore determines the host range of the retrovirus. The PA 317 cells produce retroviral particles with an amphotropic envelope protein, which can transduce cells of human and other species origin. Other packaging cell lines produce particles with ecotropic envelope proteins, which are able to transduce only mouse and rat cells.

Numerous retroviral vector constructs have been used successfully to express many foreign genes (see, e.g., Coffin, in Weiss et al. (eds.), *RNA Tumor Viruses,* 2nd ed., vol. 2 (Cold Spring Harbor Laboratory, New York, 1985, pp. 17–71). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles (Coffin, supra, 1985); however, the presence of multiple internal promoters, initially thought to be problematic (Coffin, supra, 1985), was found to be well tolerated in several retroviral constructs (Overell et al., *Mol. Cell. Biol.* 8:1803, 1983).

Retroviral vectors have been used as genetic tags by several groups to follow the development of murine hematopoietic stem cells which have been transduced in vitro with retrovirus vectors and transplanted into recipient mice (Williams et al., *Nature* 310:476, 1984; Dick et al., *Cell* 42:71, 1985; Keller et al., *Nature* 318:149, 1985). These studies have demonstrated that the infected hematopoietic cells reconstitute the hematopoietic and lymphoid tissue of the recipient animals and that the cells display a normal developmental potential in vivo. The marked cells can be visualized using any of a number of molecular biological techniques which can demonstrate the presence of the retroviral vector sequences, most notably Southern analysis and PCR (polymerase chain reaction). The ability to mark cells genetically using retroviral vectors is also useful in clinical settings in which the technique can be used to track grafts of autologous cells. This approach has already been used to track TILs (tumor-infiltrating lymphocytes) in patients given TIL therapy for terminal cancer treatment by Rosenberg et al. (*N. Engl. J. Med.* 323:570, 1990). The transduction of these cells with the marker gene was not associated with in vitro cellular dysfunction (Kasid et al., *Proc. Natl. Acad. Sci. USA* 87:473, 1990).

Many gene products have been expressed in retroviral vectors. This can either be achieved by placing the sequences to be expressed under the transcriptional control of the promoter incorporated in the retroviral LTR, or by placing them under the control of a heterologous promoter inserted between the LTRs. The latter strategy provides a way of co-expressing a dominant selectable marker gene in the vector, thus allowing selection of cells which are expressing specific vector sequences.

It is contemplated that overexpression of a stimulatory factor (for example, a lymphokine or a cytokine) may be toxic to the treated individual. Therefore, it is within the scope of the invention to include gene segments that cause the T cell clones of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the *Herpes simplex* virus type I thymidine kinase (HSV-I TK) gene (Wigler et al., *Cell* 11:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., *Proc. Natl. Acad. Sci. USA*. 89:33 (1992)).

In addition, it is useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused to form a "bifunctional selectable fusion gene" encoding a single bifunctional peptide, so that loss of one obligatorily leads to loss of the other; as described by S. Lupton et al., in Bifunctional Selectable Fusion Genes, WO 92/08796 (international publication date 29 May 1992). An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, *Mol. and Cell. Biology* 11:3374–3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See, also, S. Lupton et al., WO 92/08796, supra.

The lymphocyte clones of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, CD8+ CD4-cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician or veterinarian, and can be determined by routine examination.

The examples presented below are provided as a further guide to the practitioner of ordinary skill in the art, and are not to be construed as limiting the invention in any way.

EXAMPLE 1

Generation of CD2/CD28 and LFA-1/CD28 Chimeric Receptors

The chimeric receptors were created by fusing the extracellular domains of either CD2 or LFA-1 to the transmembrane and cytoplasmic domains of CD28.

The transmembrane and cytoplasmic domains of human CD28 (base pairs +556 to +767) was amplified by the PCR procedure. The DNA template was the human CD28 cDNA. The 5' primer employed in the PCR reaction was a single-stranded oligonucleotide comprising a sequence identical to the human CD28 sequence from position +556 to +583. The 5' primer additionally comprises a ClaI site so that the amplified fragment will contain a ClaI restriction site upstream of the CD28 sequences. The 3' primer was a single-stranded oligonucleotide comprising a sequence complementary to the human CD28 sequence from position +767 to +744. The 3' primer additionally comprises a SalI site so that the amplified fragment will contain a SalI restriction site downstream of the CD28 sequences.

PCR was conducted according to conventional procedures. The following PCR reagents were added to a 0.5 μl Eppendorf tube: 10 μl 10×PCR buffer (500 mM KCl, 100 mM Tris-HCl, pH 8.3, 25 mM MgCl$_2$, and 1 mg/ml gelatin), 10 μl of a 2.0 mM solution containing each dNTP (2 mM dATP, 2 mM dGTP, 2 mM dCTP, and 2 mM dTTP), 2 ng template, 100 pg of each oligonucleotide primer, 2.5 units of Taq DNA polymerase (Perkins-Elmer Cetus), and $H_2O$ to a final volume of 100 µl. PCR was carried out using a Gene Amp PCR System 9600 (Perkin-Elmer Cetus). The template was denatured at 94° C. for 5 minutes and PCR was carried out for 30 cycles of amplification using a step program (denaturation at 94° C., 1 minute; annealing at 54° C., 1 minute; extension at 72° C., 1 minute).

The amplified DNA fragment was resolved and recovered from a low-gelling temperature agarose gel and digested with SalI and ClaI. The fragment was re purified on a low-gelling temperature agarose gel and inserted into the SalI and ClaI sites of pBluescript (Stratagene) and named pSKcytoCD28.

The extracellular domain of CD2 (base pairs 1 to 627) was amplified by the PCR procedure. The DNA template was the human CD2 cDNA. The 5' primer employed in the PCR reaction was a single-stranded oligonucleotide comprising a sequence identical to the human CD2 sequence from position +1 to +20. The 5' primer additionally comprises an EcoRI site so that the amplified fragment will contain an EcoRI restriction site upstream of the CD2 sequences. The 3' primer employed in the PCR reaction was a single-stranded oligonucleotide comprising a sequence complementary to the human CD2 sequence from position +627 to +603. The 3' primer additionally comprises a ClaI site so that the amplified fragment will contain a ClaI restriction site downstream of the CD2 sequences.

The CD2 extracellular domain was PCR amplified as described above. The amplified fragment was resolved and recovered from a low-gelling temperature agarose gel and digested with ClaI and EcoRI. The fragment was re purified on a low-gelling temperature agarose gel and inserted into the ClaI and EcoRI sites of pSKcytoCD28 generating a single reading frame.

The CD2/CD28 chimeric receptor coding region was excised from the pBluescript backbone by digestion with BamHI (present in the polylinker region) and SalI and cloned into the BamHI and SalI sites of HyTK-CMV-Cat replacing the Cat coding sequences. The resulting construct was named HyTK-CMV-CD2/CD28.

LFA-1 is a heterodimer consisting of one subunit of each LFA-1α and LFA-1β. Chimeric receptors were generated between LFA-1α/CD28 and LFA-1β/CD28.

The 3' terminal region of the extracellular domain of LFA-1α was amplified by the PCR procedure. The DNA template was the human LFA-1α cDNA. The 5' primer was a single-stranded oligonucleotide comprising a sequence identical to the human LFA-1α cDNA from position +2961 to 2989. The 5' primer included a BamHI restriction site found in the human LFA-1α cDNA sequence from position +2961 to 2966. The 3' primer was a single-stranded oligonucleotide comprising a sequence complementary to the human LFA-1α sequence from position +3334 to +3358. The 3' primer additionally comprises an EcoRV site so that the amplified fragment will contain an EcoRV restriction site downstream of the LFA-1α sequences.

The LFA-1α sequences were amplified by PCR as described above. The amplified fragment was resolved and recovered from a low-gelling temperature agarose gel and digested with BamHI and EcoRV. The fragment was re purified on a low-gelling temperature agarose gel and inserted into the BamHI and EcoRV sites of pBluescript and named pSK3'extLFA-1α.

The human LFA-1α extracellular domain from position +1 to +2961 was excised from the human cDNA (pCDL1-a gift from T. Springer) as a BamHI restriction fragment. The DNA fragment was purified on a low-gelling temperature agarose gel and inserted into the BamHI site of pSK3'extLFA-1α, thus generating a complete extracellular domain of LFA-1α from position +1 to +3358. This construct was named pSKextLFA-1α.

The transmembrane and cytoplasmic domains of human CD28 were amplified by PCR. The DNA template was the human CD28 cDNA. The 5' primer was a single-stranded oligonucleotide comprising a sequence identical to the human CD28 sequence from position +556 to +580. The 3' primer was a single-stranded oligonucleotide comprising a sequence complementary to the human CD28 sequence from position +744 to +767. The 3' primer additionally comprises a KpnI site so that the amplified fragment will contain a KpnI restriction site downstream of the CD28 sequences.

The human CD28 transmembrane and cytoplasmic domains were PCR amplified as described above. The PCR fragment was resolved and recovered from a low-gelling temperature agarose gel, kinased, and digested with KpnI. The fragment was re purified on a low-gelling temperature agarose gel and inserted into the EcoRV (blunt) and KpnI sites of pSKcytoLFA-1α. The resulting construct was named pSKLFA-1α/CD28.

The LFA-1α/CD28 chimeric receptor was subcloned from pSKLFA-1α/CD28 as a XbaI (blunt site by fill in with Klenow) and KpnI (blunt by recess with T4 DNA polymerase) fragment. This fragment was purified on a low-gelling temperature agarose gel and inserted into the BamHI (blunt by fill in with Klenow) of tgLSplus Neo-CMV. The construct was named tgLSplusNEO-CMV-LFA-1α/CD28

The 3' terminal region of the extracellular domain of LFA-1β was amplified by the PCR procedure. The DNA template was the human LFA-1β cDNA. The 5' primer was a single-stranded oligonucleotide comprising a sequence identical to the human LFA-1β cDNA from position +1449 to +1472. The 5' primer included a NcoI restriction site found in the human LFA-1β cDNA sequence from position +1449 to +1454. The 5' primer additionally comprises a XbaI site so that the amplified fragment will contain a XbaI restriction site upstream of the LFA-1β sequences. The 3' primer was a single-stranded oligonucleotide comprising a sequence complementary to the human LFA-1β sequence from position +2048 to +2072. The 3' primer additionally comprises an EcoRV site so that the amplified fragment will contain an EcoRV restriction site downstream of the LFA-1β sequences.

The LFA-1β extracellular sequences were PCR amplified as described above. The amplified fragment was resolved and recovered on a low-gelling temperature agarose gel and digested with EcoRV and XbaI. The fragment was re purified on a low-gelling temperature agarose gel and inserted into the EcoRV and XbaI sites of pBluescript. The construct was named pSK3'extLFA-1β.

The human LFA-1β extracellular domain from position +1 to +1448 was excised from the human cDNA (pCDB1-a gift from T. Springer) as a XbaI and NcoI fragment. The restriction fragment was purified on a low-gelling temperature agarose gel and inserted into the XbaI and NcoI sites of pSK3'extLFA-1β, thus generating a complete extracellular domain of LFA-1β from position +1 to +2072. The construct was named pSKextLFA-1β.

The transmembrane and cytoplasmic domains of human CD28 were amplified by PCR. The 5' primer was a single-stranded oligonucleotide and comprised sequences identical to the human CD28 cDNA from position +556 to +580. The 3' primer was a single-stranded oligonucleotide and comprises sequences complementary to the human CD28 cDNA sequence from position +744 to +767. The 3' primer additionally comprises a SalI site so that the amplified fragment will contain a SalI restriction site downstream of the human CD28 sequences.

The CD28 sequences were PCR amplified as described above, The PCR fragment was resolved and recovered on a low-gelling temperature agarose gel, kinased, and digested with SalI. The fragment was re purified on a low-gelling temperature agarose gel and inserted into the EcoRV (blunt) and SalI sites of pSKextLFA-1β. The construct was named pSKLFA-1β/CD28.

The LFA-1β/CD28 sequences were excised from pSKLFA-1β/CD28 by digestion with XbaI (blunt by fill in with Klenow) and SalI. The fragment was purified on a low-gelling temperature agarose gel and inserted into the BamHI (blunt by fill in with Klenow) and SalI sites of HyTK-CMV-Cat replacing the Cat sequences. The construct was named HyTK-CMV-LFA-1β/CD28.

EXAMPLE 2

Generation of Viral Producing Lines

To derive stable PA317 cell lines producing amphotrophic HyTK-CMV-CD2/CD28, tgLSplusNeo-CMV-LFA-1α/CD28 and HyTK-CMV-LFA-1β/CD28 viral particles, the retroviral plasmid DNAs were first transfected into ψ2 ecotropic cells (Mann et al., 1983). ψ2 cells were grown in DMEM supplemented with 10% bovine calf serum, 2 mM L-glutamine, 50 U/ml penicillin, and 50 μg/ml streptomycin at 37° C. in a humidified atmosphere supplemented with 10% $CO_2$. For transfection, exponentially growing cells were harvested by trypsinization, washed free of serum with PBS, and resuspended in serum-free DMEM at a concentration of $10^7$ cells/ml. Plasmid DNA (20 μg) was added to 800 μl of cell suspension ($8 \times 10^6$ cells) and the mixture subjected to electroporation using the Biorad GENE PULSER and CAPACITANCE EXTENDER (200 volts and 960 μFa in a 0.4 cm electrode gap). The transfected ψ2 cells were then transferred to a 10-cm tissue culture dish containing 10 ml complete growth medium supplemented with 10 mM sodium butyrate, and allowed to attach overnight. After 15 hours, the medium was removed and replaced with 15 ml of fresh medium. After a further 24 hours, the medium containing the transiently produced ecotropic virus particles was harvested, centrifuged at 3000 rpm for 10 minutes, and used to infect PA317 amphotrophic packaging cells (Miller and Buttimore, 1986). PA317 cells were grown in DMEM supplemented with 10% fetal bovine serum, 2 mM L-glutamine, 50 U/ml penicillin, and 50 μg/ml streptomycin at 37° C. in a humidified atmosphere supplemented with 10% $CO_2$. Exponentially dividing PA317 cells were plated at a density of $1.5 \times 10^6$ cells/10-cm tissue culture dish and allowed to attach overnight. The following day, the medium was removed and replaced with serial dilution of the virus-containing supernatant (6 ml/dish) in medium supplemented with 4 μg/ml polybrene. Infection was allowed to proceed overnight and then the supernatant was replaced with 15 ml complete growth medium. Infected cells were selected for drug resistance after a further 8 hours of growth by adding 500 μg/ml hygromycin B or 1 mg/ml G418. Drug resistant colonies were isolate 12–18 days later and individually expanded. The cells were subjected to Southern analysis to determine the integrity of the retroviral provirus and the copy number. The production of retroviral particles was measured by titering on NIH 3T3 cells using standard techniques (Ausubel et al., 1987). Clones that contained a single unrearranged retroviral provirus and produced a high titer of infectious retroviral particles were used to infect T cells.

EXAMPLE 3

Cell Surface Expression of the CD2/CD28 Chimeric Receptor in NIH 3T3 Cells

NIH 3T3 cells were infected with the amphotropic viral supernatant for the HyTK-CMV-CD2/CD28 chimeric receptor. The NIH 3T3 cells were plated in 6 well tissue culture plates at a density of $2.5 \times 10^4$ cells/well and allowed to attach overnight. The next day, the medium was removed and replaced with a 1/10 dilution of viral supernatant in complete medium supplemented with 4 μg/ml polybrene. Infection was allowed to proceed overnight. The supernatant was removed after 15 hours and replaced with fresh medium. Four hours later the medium was replaced with medium containing 350 units/ml hygromycin B. The polyclonal population which survived drug selection was expanded and utilized for flow cytometry analysis for surface expression of human CD2.

Infected and uninfected NIH3T3 cells were released from the tissue culture flask by treatment with 2% EDTA. Cells were washed twice with PBS, counted and $1 \times 10^6$ cells transferred to a FACS tube in 1 ml FACS buffer (PBS supplemented with 1% bovine calf serum and 0.02% sodium azide). The cells were pelleted and the supernatant decanted. The cells were resuspended in residual supernatant (100 μl). Anti-human CD2 (35.1 hybridoma supernatant) was added in a volume of 50 μl and incubated on ice for 30 minutes. The cells were next washed twice with 1 ml of FACS buffer and then anti-mouse FITC added and incubated on ice for 30 minutes. The cells were washed twice with 1 ml FACS buffer and then resuspended in 0.5 ml FACS buffer, fixed with an equal volume of 3% paraformaldehyde and analyzed on a Becton Dickenson FACScan. Controls were performed with exposure to no antibody or anti-mouse FITC alone. Only the infected NIH 3T3 cells had surface human CD2 expression demonstrating that the chimeric receptor was expressed properly on the cell surface.

EXAMPLE 4

Signaling of the CD2/CD28 chimeric receptor in EL-4 cells

EL-4 cells are a murine lymphoma cell line and was grown in RPMI 1640 supplemented with 10% fetal bovine serum, 2 mM L-glutamine, 50 U/ml penicillin, and 50 μg/ml streptomycin at 37° C. in a humidified atmosphere supplemented with 10% $CO_2$. For transfection, exponentially growing cells were pelleted and resuspended in serum-free RPMI at a concentration of $5 \times 10^6$ cells/ml. HyTK-CMV-CD2/CD28 DNA (10 μg) was added to 800 μl of cell suspension ($4 \times 10^6$ cells) and subjected to electroporation using the Biorad Gene Pulser and Capacitance Extender (300 V and 960 μFa in a 0.4 cm electrode gap). The transfected cells were transferred to a 25 cm flask in 10 ml complete media and allowed to recover overnight. After 24 hours, the cells were plated in 96 well plates at cell densities of 2000, 1000, 500, 250, and 125 cells per well under hygromycin B selection (750 units/ml). After 12–15 days, colonies were picked and expanded. Cells were analyzed for cell surface expression of human CD2 by flow cytometry as described in Example 3. One of the positive clones (clone 5) was expanded for analyses.

To determine if the chimeric CD2/CD28 receptor could signal upon engagement and induce IL-2 in the EL-4 cells, EL-4 clone 5 cells were stimulated with various antibodies. The antibodies and the concentrations used are listed below:
(1) anti-mouse CD28 (0.5, 1.0, 5.0, and 10.0 µg/ml)
(2) anti-human CD2 (0.5, 1.0, 5.0, and 10.0 µg/ml)
(3) anti-mouse CD3 (5.0 µg/ml)
(4) anti-mouse CD3 (5.0 µg/ml) and anti-mouse CD28 (0.5, 1.0, 5.0, 10.0 µg/ml)
(5) anti-mouse CD3 (5.0 µg/ml) and anti-human CD2 (0.5, 1.0, 5.0, 10.0 µg/ml).

The assay was set up in triplicate in 96 well round bottom plates. The appropriate antibody or combination of antibodies was added in a volume of 30 µl PBS per well and incubated at 37° C. for 2 hours. The plates were washed 3 times with PBS and then $2 \times 10^4$ EL-4 clone 5 cells were added in 0.2 ml complete RPMI medium. The plates were incubated for 24 hours at 37° C. and then 100 µl supernatant was transferred from each well to 96 well flat bottom plates. IL-2 induction was determined by the IL-2 bioassay as follows. CTLL-2 cells ($4 \times 10^3$ cells/well) were added to each of the supernatants in a volume of 100 µl complete medium. CTLL-2 cells are dependent upon IL-2 for growth. The CTLL-2 cells were incubated in the presence of the EL-4 supernatants for 24 hours at 37° C. and during the last 4 hours of incubation 0.5 µCi of $^3$H-thymidine was included. Cultures were harvested on a Packard Filtermate 196 and tritium incorporation determined on a Packard Matrix 96 direct beta counter. Counts per minute (CPM shown in FIG. 7) are means from triplicate cultures.

Figure 7:
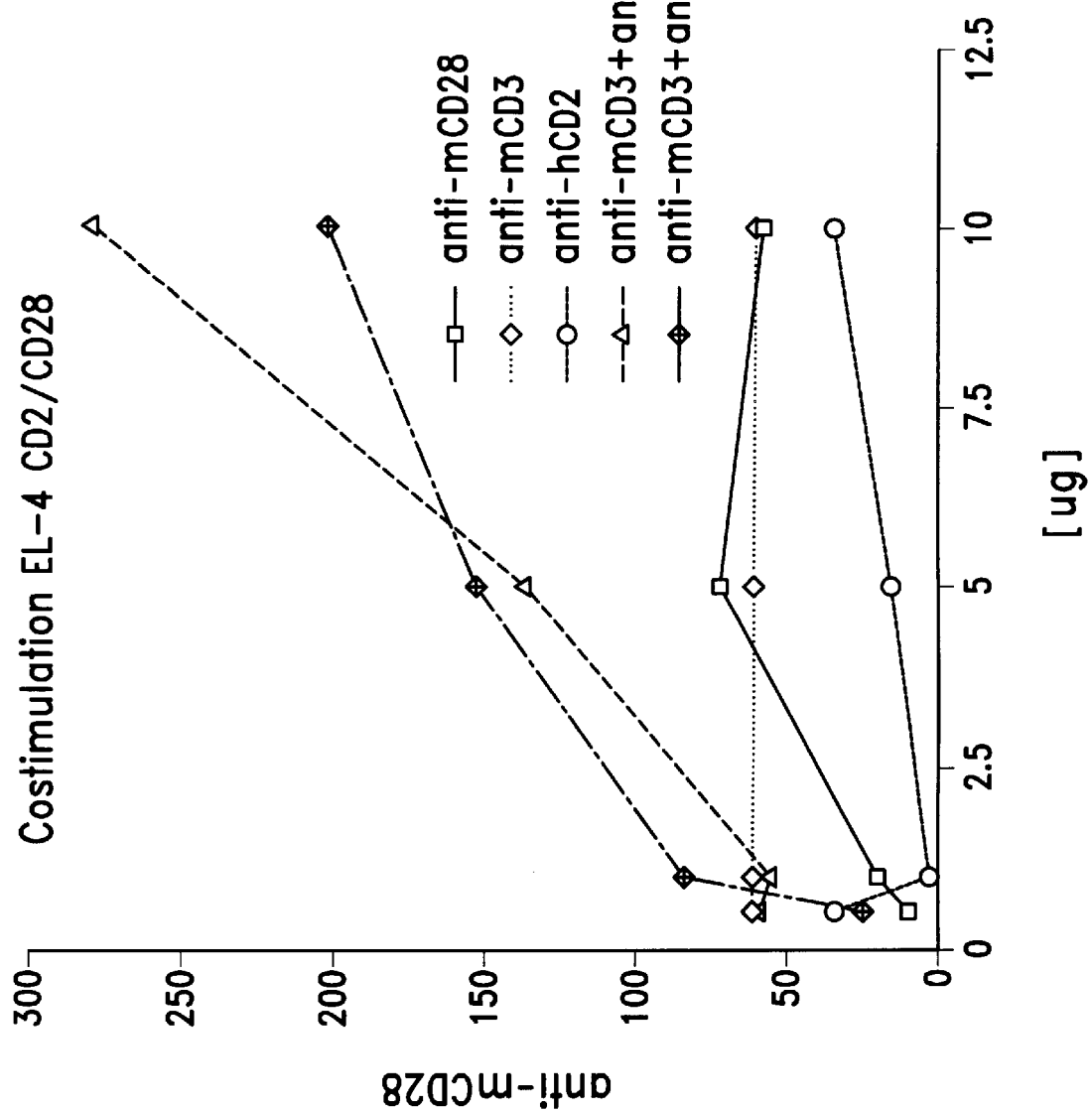
FIG. 7 is a graph illustrating the results of a EL-4 clone 5 co-stimulation experiment described in Example 4.
Figure 8A:
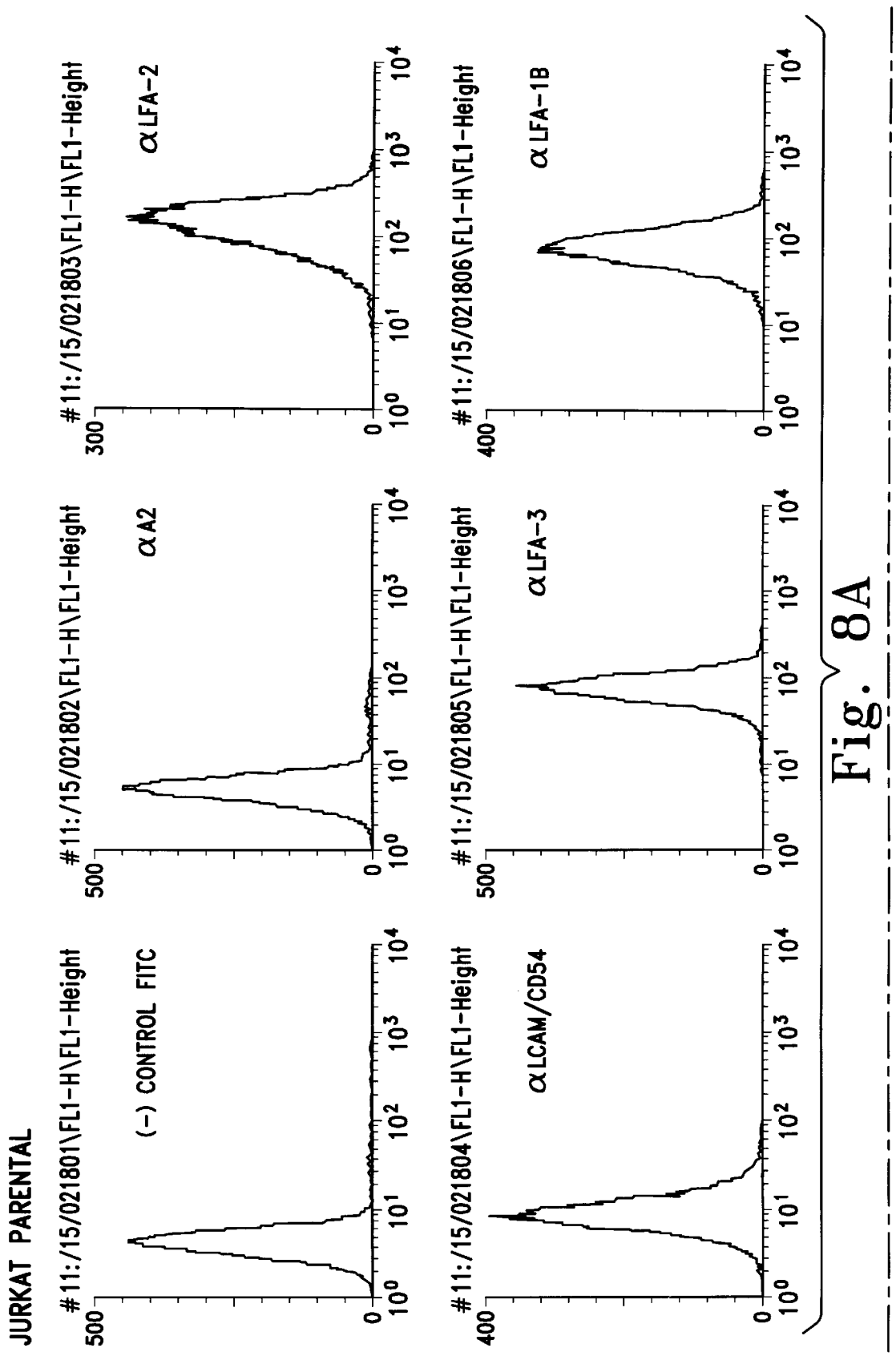
Figure 8B:
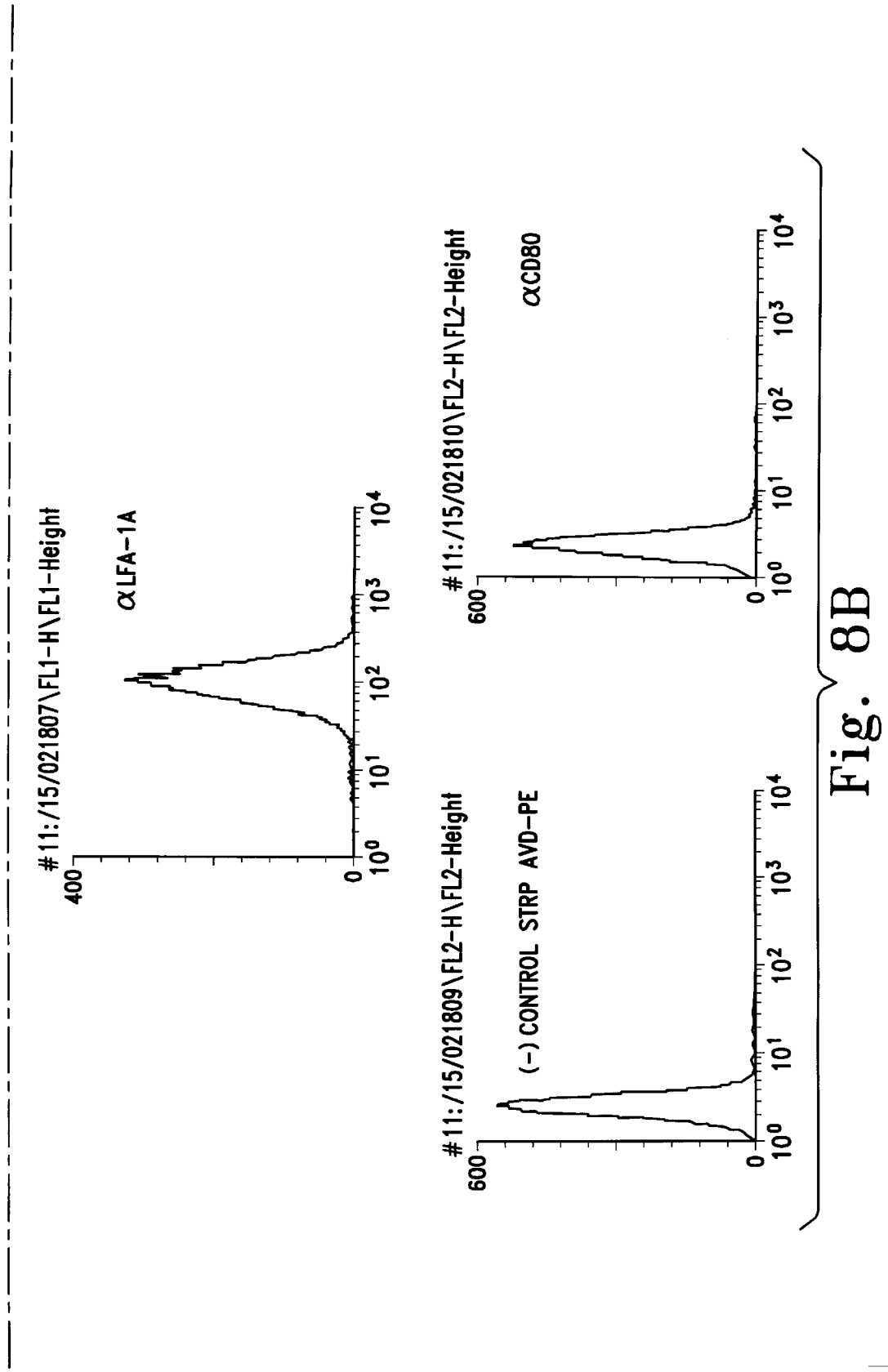
Figure 8C:
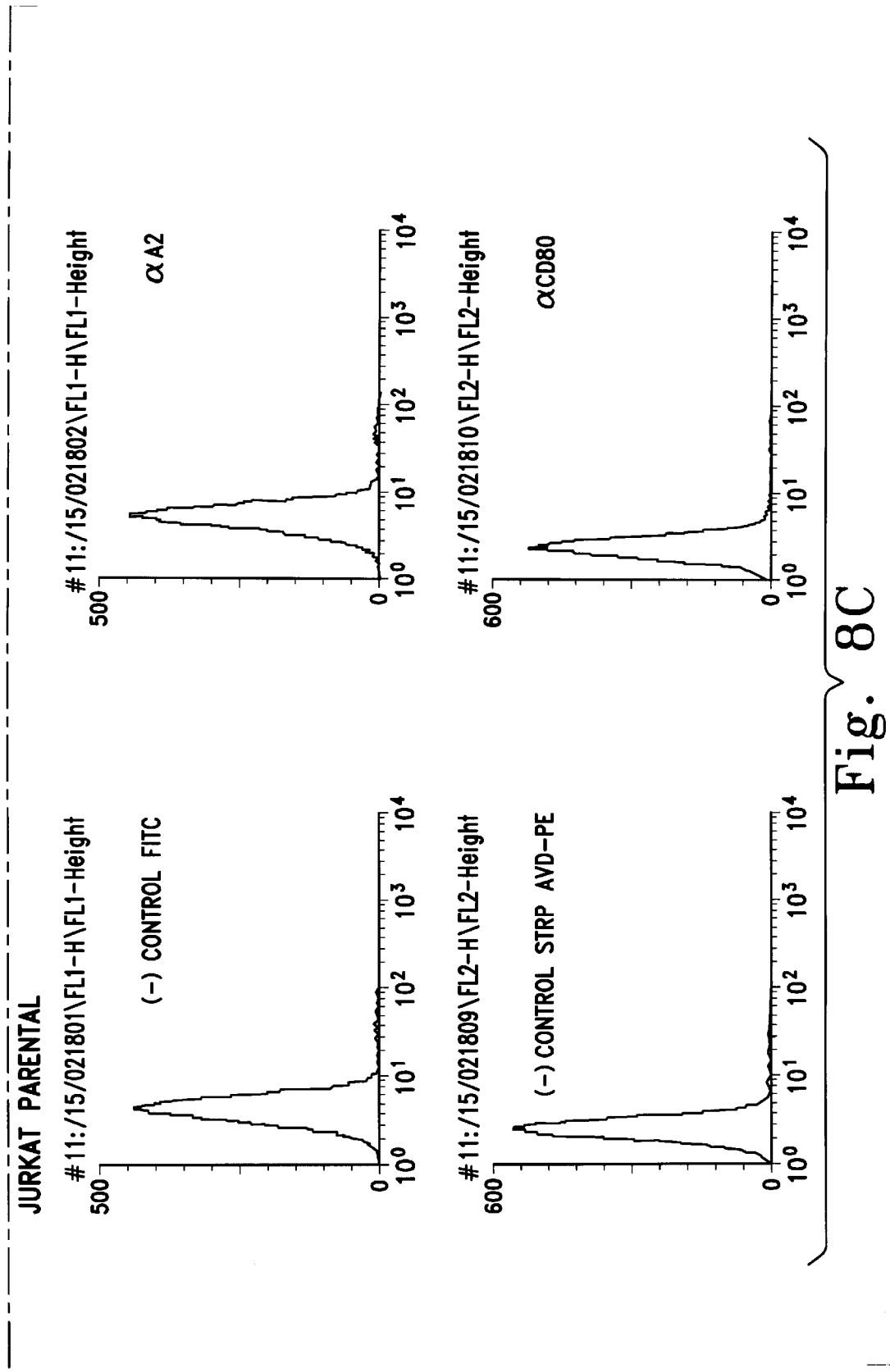
Figure 9B:
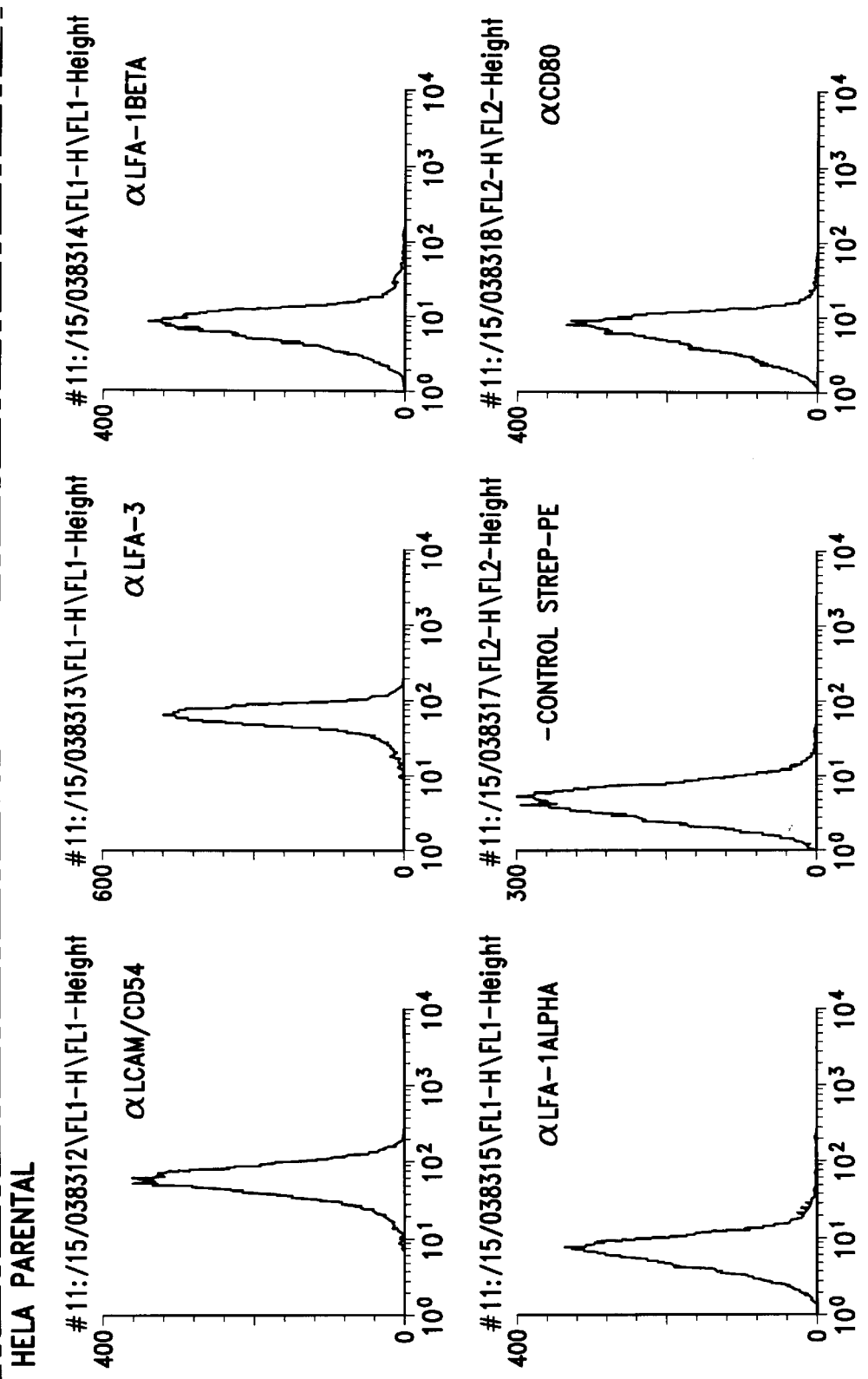
Figure 9C:
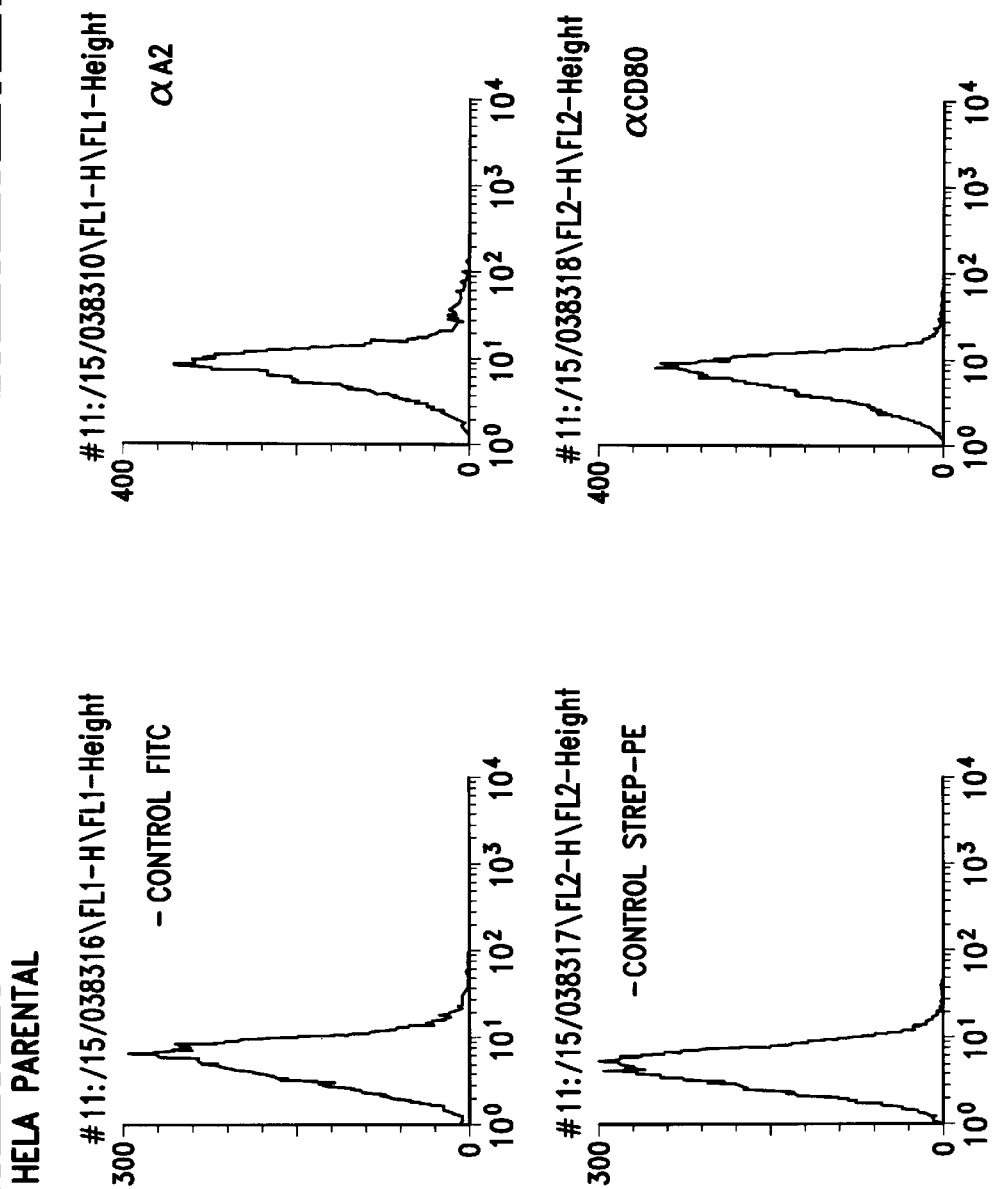
Figure 9D:
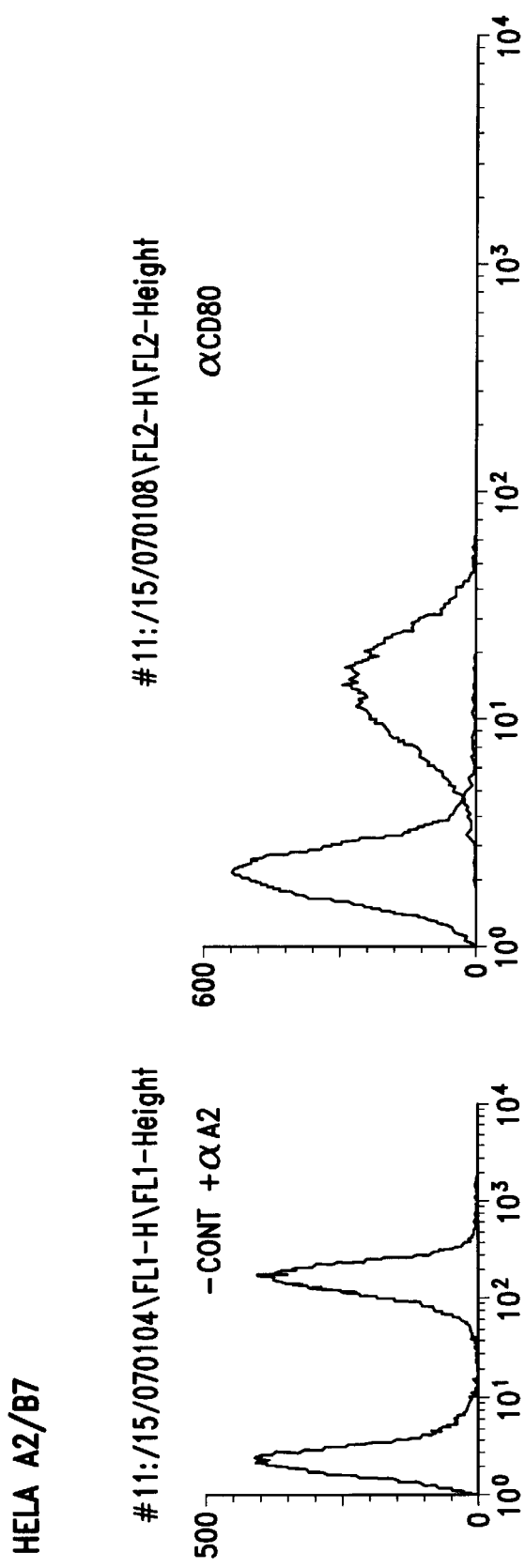

Anti-mouse CD3, anti-mouse CD28 and the anti-human CD2 alone were unable to induce IL-2 production in the EL-4 clone 5 cells at the concentrations used. The combination of anti-mouse CD3 and anti-mouse CD28 or anti-mouse CD3 and anti-human CD2 were capable of inducing IL-2 production in the EL-4 clone 5 cells (FIG. 7).

EXAMPLE 5

Generation of Human HLA-A2 Alloreactive and HLA-A2 Flu Nucleoprotein (NP) Specific CTL Clones CTL clones were generated by limiting dilution of primary CTL cultures. Briefly, primary CTL cultures were established by culturing $5 \times 10^6$ freshly isolated responder peripheral blood mononuclear cells ("PBMC") (HLA-A2 negative donor for A-2 reactive CTL and HLA-2 positive donor for the HLA-A2 Flu NP peptide clones, respectively) with $5 \times 10^6$ irradiated (3500 rad) PBMC (HLA-A2 positive and autologous HLA-A2 positive, respectively) in RPMI complete media with 10% FBS. For HLA-A2 Flu NP reactive CTL, $10^{-4}$M flu nucleoprotein (NP) peptide (peptide sequence: KGILGFVFTLTV) (SEQ. ID No: 4) was included in the reaction. Cultures were incubated for 7 days at 37° C., 10% $CO_2$. On day 7 primary cultures were cloned by limiting dilution in 96-well round bottom microtiter plates in 17 units/ml IL-2 (Cetus), and $5 \times 10^{-5}$M peptide where appropriate. Wells contained the appropriate number of responder cells (cells from the primary culture) stimulated with $1 \times 10^5$ irradiated filler cells of the appropriate haplotype. Weekly for 3 weeks 100 µl of supernatant of the total 200 µl volume was removed and replaced with 100 µl of fresh medium containing irradiated stimulators as above. On week 3, one-half of the culture was removed and tested in a standard $^{51}$Cr release assay. Clones positive for lytic activity were picked by Poisson statistics and expanded for use.

EXAMPLE 6

Generation of Jurkat and HeLa A2+ and A2-B7-1+ Antigen Presenting Cells

Jurkat and HeLa cells were analyzed by flow cytometry for cell surface expression of A2, B7-1, ICAM-1, and LFA-3. Both cell types were positive for ICAM-1 and LFA-3 but were negative for A2 and B7-1. Jurkat cells were transfected with a plasmid construct RSV.A2 as described for EL-4 cells in Example 4. Cells were placed under G418 selection (1 mg/ml) and after 14 days clones were picked and expanded. The clones were analyzed for the presence of A2 on the cell surface by flow cytometry. Clone 6 had high levels of A2 expression and was chosen for further analyses. A portion of clone 6 was used for transfection with a retroviral construct B7-1-IRES-HyTK. Transfection conditions were as described in Example 4 for EL-4 cells. Cells were placed under hygromycin B selection (350 units/ml) and clones picked after 10–14 days. Clones were analyzed by flow cytometry for the presence of cell surface B7-1 expression.

HeLa cells were trypsinized, counted and resuspended in medium at a concentration of $5 \times 10^6$ cells/ml. The HeLa cells were transfected with RSV.A2 as described for EL-4 cells in Example 4. Cells were plated in 10-cm tissue culture plates and after 24 hours were placed under G418 selection at a concentration of 0.6 mg/ml. Clones were picked, expanded and analyzed by flow cytometry. Clone 17 was chosen for further analysis due to high expression of cell surface A2. A portion of clone 17 was transfected with the same B7-1 construct as Jurkat cells and transfection conditions were as described in Example 4. Cells were plated in 10-cm dishes and selected with 0.5 mg/ml hygromycin B. Clones were expanded and analyzed by flow cytometry for B7-1 expression. HeLa clone 10 displayed high levels of expression of both A2 and B7-1.

EXAMPLE 7

Co-stimulation of A2 Alloreactive CTL with Jurkat A2 and Jurkat A2-B7-1

The antigen presenting cells (APCs) generated in Example 6 were tested as stimulators of a A2 specific alloreactive CTL to determine conditions under which the CD28 pathway is required for activation of the CTL (the APC must express B7-1). The stimulator cells, Jurkat/A2, Jurkat/A2-B7-1, HMY.CIR/A2-B7-1 (positive control), and in negative PBMCs were irradiated at 3,500 rads. A2 specific alloreactive T cells were plated in 24 well plates at a density of $3 \times 10^5$ cells/well. Stimulator cells were added at the concentrations listed below:
(1) HMY.CIR/A2-B7-1 ($3 \times 10^5$) plus A2 negative PBMCs ($5 \times 10^6$);
(2) Jurkat/A2 ($5 \times 10^6$);
(3) Jurkat/A2-B7-1 ($5 \times 10^6$)

The total volume of medium (complete RPMI medium supplemented with 17 U/ml IL-2) was 2 ml per well. Cells were assayed for CTL activity by the chromium release assay on day 5. Briefly, CTLs were resuspended in complete medium, counted, and then added to cultures in the indicated Effector:Target (E:T) ratios. $5 \times 10^5$ target cells were pelleted and resuspended in 0.1 ml medium and incubated with 0.2 ml $^{51}$Cr (200 mCi) for 1 hour at 37° C. Cells were washed 3 times in medium and the assay set up in 96 well "v" bottom plates. Target cells ($1 \times 10^3$ cells/well) in triplicate cultures, were either HMY.CIR (A2 negative) or HMY.CIR/A2-B7-1 positive cells. Free isotope was collected with a Skatron harvest system and counted on a Packard Cobra II auto gamma counter. The spontaneous release of $^{51}$Cr was determined by incubation of targets in medium alone and maximum $^{51}$Cr release was determined by lysis of target cells with 2% triton X-100. The percent specific lysis was calculated as follows:

% specific lysis=[(experimental value spontaneous release) divided by (maximum value spontaneous release)] times 100%.

Effector to target ratios (E:T) were as indicated in Table 1.

TABLE 1

$^{51}$Cr Release Assay

| Effector Stimulated with: | E:T ratio | Target | % Specific Lysis |
|---|---|---|---|
| HMY.CIR/A2-B7-1 + PBMC | 40:1 | HMY.CIR/B7-1 | 5.5 |
|  | 20:1 |  | 6.4 |
|  | 10:1 |  | 3.1 |
|  | 5:1 |  | 4.3 |
| Jurkat/A2 | 40:1 | HMY.CIR/B7-1 | 1.1 |
|  | 20:1 |  | 1.9 |
|  | 10:1 |  | 1.9 |
|  | 5:1 |  | 1.5 |
| Jurkat/A2-B7-1 | 40:1 | HMY.CIR/B7-1 | 4.0 |
|  | 20:1 |  | 8.4 |
|  | 10:1 |  | 4.7 |
|  | 5:1 |  | 4.8 |
| HMY.CIR/A2-B7-1 + PBMC | 40:1 | HMY.CIR/A2-B7-1 | 53.0 |
|  | 20:1 |  | 48.5 |
|  | 10:1 |  | 26.1 |
|  | 5:1 |  | 19.5 |
| Jurkat/A2 | 40:1 | HMY.CIR/A2-B7-1 | 0.0 |
|  | 20:1 |  | 0.0 |
|  | 10:1 |  | 0.0 |
|  | 5:1 |  | 0.0 |
| Jurkat/A2-B7-1 | 40:1 | HMY.CIR/A2-B7-1 | 56.3 |
|  | 20:1 |  | 29.0 |
|  | 10:1 |  | 25.2 |
|  | 5:1 |  | 4.3 |

EXAMPLE 8

Modification of CTL by Chimeric Receptor

The proviral structure of the chimeric receptors are as depicted in FIG. 1. PA317 amphotropic retroviral producer clones were generated and characterized as described in Example 2.

The A2 specific alloreactive and flu matrix peptide specific CD8+ CTL are generated as described in Example 5. The clones are transduced with either the HyTK-CMV-CD2/CD28 retrovirus or the tgLSplus NEO-cmv-LFA-1α/CD28 and HyTK-CMV-LFA-1β/CD28 retroviruses in the following manner. $3 \times 10^5$ CTLs are incubated with $5 \times 10^6$ irradiated A2+ PBMCs in 2 ml complete medium (RPMI) in 24 well plates. Two days after stimulation, media is removed and replaced with 2 ml viral supernatant with 10 U/ml IL-2 (Cetus), and 10 µg/ml DEAE-dextran. Cultures are incubated for 24 hours at 37°C. The infection is allowed to proceed for 24 hours. The cells are then harvested and plated in a limiting dilution assay (LDA) under the appropriate drug selection. On day 7 the LDAs are stimulated with $1 \times 10^5$ irradiated PBMCs.

CD8+ T cell clones transduced with the above retroviral vectors are plated in 96 well plates along with Jurkat A2 or HeLa A2 as stimulator cells. Varying amounts of flu peptide is included in the well to provide antigen stimulation. The concentration of peptide required for stimulation of parental and modified T cells is determined. Exogenous IL-2 is added in varying quantities (in addition to a no IL-2 sample). After 7 days, cells are harvested and viable cell numbers are determined by trypan blue exclusion. T cells are then restimulated as above and long term growth kinetics determined for each growth condition. IL-2 induction in the cultures without exogenously added IL-2 is determined by the IL-2 bioassay as described in Example 4. Bulk cultures are set up in 24 well plates (as in Example 7) to assay the ability of the cells to specifically kill target cells in the absence of stimulation via B7.

EXAMPLE 9

Initiation of the CD28 Signaling Pathway by Chimeric Receptors in Murine and Human Cells One of the earliest events in the CD28 signaling pathway is believed to be the association of the p85 subunit of PI3-kinase with the cytoplasmic domain of CD28 upon CD28 stimulation (see, e.g., Prasad, et al., *PNAS*, 91:2834, 1994; Lu et al., *Eur. J. Immunol.* 24:2732, 1994; and Pages et al., *Nature*, 369:327, 1994). The p85 subunit has been shown to associate with the Y(P)MXM motif within the cytoplasmic domain of CD28, and this association is apparently required for CD28 signaling (Prasad et al, ibid 1994; Pages et al., ibid 1994).

The following experiment confirmed that chimeric receptors prepared as described above retained the ability to engage in this early event in CD28 signaling.

Briefly, various cell lines expressing CD2/CD28 chimeric receptors (as described above) were analyzed to determine if the p85 subunit of PI3-kinase associated with the cytoplasmic domain of the chimeric receptor upon stimulation through the CD2 extracellular domain.

A first set of experiments involved a murine lymphoma cell line, EL-4, as described in Example 4. $100 \times 10^6$ of either EL-4 parental or EL-4 cells expressing the chimeric receptor were pelleted and resuspended in 2.0 ml of serum free RPMI 1640 media. 0.5 ml of cells was added to four wells of a twelve well plate and treated as follows. Two wells were unstimulated, one well was stimulated with 10 µg/ml anti-human CD2, and one well was stimulated with 10 µg/ml anti-murine CD28. The cells were stimulated for 3 minutes at 37° C. and then 1 µg/ml goat anti-mouse IgG or goat anti-hamster IgG was added respectively. After incubation for 20 minutes at 37° C. the cells were pelleted and lysed in NP-40 buffer (10 mM Tris pH 7.5, 150 mM NaCl and 1% NP-40) for 30 minutes on ice. The nuclei were then pelleted by centrifugation at 14,000 g for 5 minutes at 4° C. The supernatant was transferred to a new tube and immunoprecipitations performed. Cells stimulated with antibodies were immunoprecipitated with the same antibodies and the unstimulated samples were precipitated with either anti-human CD2 or anti-murine CD28. Immunoprecipitates were collected using Protein G, washed 2–3 times and then resolved on a 10% acrylamide gel. After transfer to immobilon P, a Western blot for the p85 subunit of PI3-kinase was performed as previously described (Lu et al., ibid 1994). A cell lysate was also run as a positive control for the detection of p85. The p85 subunit was also run as a positive control for the detection of p85.

As expected, the p85 subunit was co-immunoprecipitated from EL-4 parental cells only upon stimulation with anti-murine CD28. In contrast, for EL-4 cells expressing the CD2/CD28 chimeric receptor, stimulation with either anti-murine CD28 or anti-human CD2 resulted in co-immunoprecipitation of p85. These results provided confirmatory evidence that the chimeric receptor retained functionality for CD28 signaling in that the first known step of the CD28 signaling pathway was initiated upon stimulation of the chimeric receptor using anti-CD2 antibody.

Similar analyses were performed using a human T cell line, Hut 78; essentially as described above. In this case, stimulations were performed with either anti-human CD28 or anti-human CD2. Again, as expected, the p85 subunit was co-immunoprecipitated from Hut 78 parental cells only upon CD28 stimulation but not CD2 stimulation. In contrast, for Hut 78 cells expressing the CD2/CD28 chimeric receptor, stimulation with either CD28 or CD2 resulted in co-immunoprecipitation of p85; analogous to the results observed using the murine cells. These results provided additional confirmatory evidence that the chimeric receptor retained functionality for CD28 signaling in that the first known step of the CD28 signaling pathway was initiated upon stimulation of the chimeric receptor in human cells using anti-CD2 antibody.

We claim:

1. A cytotoxic T lymphocyte (CTL) comprising a chimeric cell surface receptor, said chimeric receptor comprising a fusion polypeptide of the following structure:

XC—TM—IC28 wherein (XC) is an extracellular region derived from a receptor for a ligand (L) that is expressed on the surface of an antigen-displaying cell, fused via a transmembrane region (TM) to an intracellular region (IC28) which is derived from the intracellular region of the CD28 receptor, wherein the antigen displaying cell displays an antigen in association with class I MHC.

2. A CTL of claim 1, wherein said CTL is selected from the group consisting of antigen-specific CD8 positive pre-CTLs and antigen-specific CD8 positive effector-CTLs.

3. A CTL of claim 1, wherein both the transmembrane region (TM) and the intracellular region (IC28) are derived from the CD28 receptor.

4. A CTL of claim 2, wherein L is a ligand that is expressed on the surface of human cells.

5. A CTL of claim 2, wherein L is a ligand that is expressed on the surface of a subset of human cells.

6. A CTL of claim 2, wherein L is a ligand that mediates adhesion between a CTL and a human cell.

7. A CTL of claim 2, wherein XC is derived from the extracellular region of a monomeric receptor.

8. A CTL of claim 7, wherein said monomeric receptor is a CD2 cell surface molecule.

9. A CTL of claim 2, wherein the chimeric receptor is a complex comprising at least two fusion polypeptides, each fusion polypeptide comprising an XC region derived from an individual polypeptide chain of an oligomeric receptor, fused via a TM region to an intracellular region derived from the CD28 receptor.

10. A CTL of claim 9, wherein said oligomeric receptor is a member of the integrin family of heterodimeric cell surface proteins.

11. A CTL of claim 10, wherein said oligomeric receptor is an LFA-1 cell surface molecule, and the chimeric receptor comprises two fusion polypeptides, one of which has an XC region derived from the alpha chain of LFA-1 and the other of which has an XC region derived from the beta chain of LFA-1.

12. A method of using a CTL of claim 1 to mediate lysis of a target cell bearing a cognate antigen, comprising allowing said CTL to come into contact with a target cell bearing a cognate antigen.

* * * * *